(12) United States Patent
Gerhard et al.

(10) Patent No.: US 7,345,301 B2
(45) Date of Patent: Mar. 18, 2008

(54) MIXTURES OF MATRIX MATERIALS AND ORGANIC SEMICONDUCTORS CAPABLE OF EMISSION, USE OF THE SAME AND ELECTRONIC COMPONENTS CONTAINING SAID MIXTURES

(75) Inventors: Anja Gerhard, Veitschöchheim (DE); Horst Vestweber, Gilserberg (DE); Philipp Stössel, Frankfurt (DE); Susanne Heun, Bad Soden (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 258 days.

(21) Appl. No.: 10/553,114

(22) PCT Filed: Apr. 13, 2004

(86) PCT No.: PCT/EP2004/003861

§ 371 (c)(1),
(2), (4) Date: Oct. 14, 2005

(87) PCT Pub. No.: WO2004/093207

PCT Pub. Date: Oct. 28, 2004

(65) Prior Publication Data

US 2006/0208221 A1    Sep. 21, 2006

(30) Foreign Application Priority Data

Apr. 15, 2003 (DE) ............................ 103 17 556
Nov. 25, 2003 (DE) ............................ 103 55 358

(51) Int. Cl.
*H01L 51/46* (2006.01)
*H01L 51/54* (2006.01)
*C09K 11/06* (2006.01)

(52) U.S. Cl. .......... 257/40; 257/E51.027; 257/E51.018; 252/301.16; 540/1; 544/1

(58) Field of Classification Search ............... 257/40, 257/E51.027, E51.018; 252/301.16; 540/1; 544/1
See application file for complete search history.

(56) References Cited

U.S. PATENT DOCUMENTS

| 4,539,507 | A | 9/1985 | VanSlyke et al. |
|---|---|---|---|
| 5,151,629 | A | 9/1992 | VanSlyke |
| 5,621,131 | A | 4/1997 | Kreuder et al. |
| 5,679,760 | A | 10/1997 | Mullen et al. |
| 5,763,636 | A | 6/1998 | Kreuder et al. |
| 6,653,438 | B1 | 11/2003 | Spreitzer et al. |
| 2001/0053462 | A1 | 12/2001 | Mishima |
| 2004/0077862 | A1 | 4/2004 | Stossel et al. |
| 2004/0133004 | A1 | 7/2004 | Stossel et al. |
| 2004/0135131 | A1 | 7/2004 | Treacher et al. |

(Continued)

FOREIGN PATENT DOCUMENTS

DE    102 38 903    3/2004

(Continued)

*Primary Examiner*—Evan Pert
(74) *Attorney, Agent, or Firm*—Connolly Bove Lodge Hutz LLP

(57) ABSTRACT

The present invention describes new types of material mixtures composed of at least two substances, one serving as a matrix material and the other being an emission material capable of emission, the latter comprising at least one element of atomic number greater than 20, and the use thereof in organic electronic components such as electroluminescent elements and displays.

21 Claims, 4 Drawing Sheets

U.S. PATENT DOCUMENTS

| | | |
|---|---|---|
| 2004/0138455 A1 | 7/2004 | Stossel et al. |
| 2005/0131232 A1 | 6/2005 | Stössel et al. |
| 2005/0176958 A1 | 8/2005 | Stössel et al. |

FOREIGN PATENT DOCUMENTS

| | | |
|---|---|---|
| EP | 0 707 020 | 4/1996 |
| EP | 0 842 208 | 5/1998 |
| EP | 0 894 107 | 2/1999 |
| EP | 1 028 136 | 8/2000 |
| EP | 1 191 612 | 3/2002 |
| EP | 1 191 613 | 3/2002 |
| EP | 1 191 614 | 3/2002 |
| EP | 1 202 358 | 5/2002 |
| JP | 6-192654 | 7/1994 |
| WO | WO-92/18552 | 10/1992 |
| WO | WO-00/22026 | 4/2000 |
| WO | WO-00/70655 | 11/2000 |
| WO | WO-01/41512 | 6/2001 |
| WO | WO-02/02714 | 1/2002 |
| WO | WO-02/15645 | 2/2002 |
| WO | WO-02/060910 | 8/2002 |
| WO | WO-02/068435 | 9/2002 |
| WO | WO-02/077060 | 10/2002 |
| WO | WO-02/081488 | 10/2002 |
| WO | WO-03/040160 | 5/2003 |
| WO | WO-03/074628 | 9/2003 |
| WO | WO-03/084972 | 10/2003 |
| WO | WO-03/099959 | 12/2003 |
| WO | WO-04/013080 | 2/2004 |

Open circles: CBP; solid line: bis(9,9'-spirobifluoren-2-yl) ketone

MIXTURES OF MATRIX MATERIALS AND ORGANIC SEMICONDUCTORS CAPABLE OF EMISSION, USE OF THE SAME AND ELECTRONIC COMPONENTS CONTAINING SAID MIXTURES

RELATED APPLICATIONS

This application is a national stage application (under 35 U.S.C. 371) of PCT/EP2004/003861 filed Apr. 13, 2004 which claims benefit to German application 103 17 556.3 filed Apr. 15, 2003 and German application 103 55 358.4 filed Nov. 25, 2003.

The present invention relates to the use of novel materials and material mixtures in organic electronic components such as electroluminescent elements, and to the use thereof in displays based thereon.

In a series of different types of applications which can be classified within the electronics industry in the widest sense, the use of organic semiconductors as active components (=functional materials) has become reality in recent times or is expected in the near future. For instance, light-sensitive organic materials (e.g. phthalocyanines) and organic charge transport materials (generally triarylamine-based hole transporters) have already found use for several years in copying machines. The use of specific semiconducting organic compounds which are capable of emission of light in the visible spectral region is just starting to be introduced onto the market, for example in organic electroluminescent devices. Their individual components, the organic light-emitting diodes (OLEDs), have a very wide spectrum of application as:

1. white or colored backlighting for monochrome or multi-color display elements (for example in pocket calculators, for mobile telephones and other portable applications),
2. large-surface area displays (for example traffic signs, billboards and other applications),
3. illumination elements in all colors and forms,
4. monochrome or full-color passive matrix displays for portable applications (for example mobile telephones, PDAs, camcorders and other applications),
5. full-color, large-surface area, high-resolution active matrix displays for a wide variety of applications (for example mobile telephones, PDAs, laptops, televisions and other applications).

The development of some of these applications is already very, far advanced; nevertheless, there is still great technical need for improvement.

Devices containing relatively simple OLEDs have already been introduced onto the market, as demonstrated by the car radios from Pioneer or a digital camera from Kodak with an organic display. However, there are still considerable problems which are in need of urgent improvement:

1. For instance, the operative lifetime in particular of OLEDs is still low, so that it has only been possible to date to commercially realize simple applications.
2. Although the efficiencies of OLEDs are acceptable, even improvements are still desired here too, specifically for portable applications.
3. The color coordinates of OLEDs, especially in the red, are not good enough. Particularly the combination of good color coordinates with high efficiency has to be improved.
4. The aging processes are generally accompanied by a rise in the voltage. This effect makes voltage-driven organic electroluminescent devices, for example displays or display elements, difficult or impossible. However, voltage-driven addressing is more complex and costlier precisely in this case.
5. The required operating voltage is quite high specifically in the case of efficient phosphorescent OLEDs and therefore has to be reduced in order to improve the power efficiency. This of great significance specifically for portable applications.
6. The required operating current has likewise been reduced in the last few years, but has to be reduced still further in order to improve the power efficiency. This is particularly important specifically for portable applications.
7. The multitude of layers makes the construction of OLEDs complex and technologically very complicated. It would therefore be desirable to be able to realize OLEDs with a simpler layer structure which requires fewer layers, but still has good or even improved properties.

The reasons mentioned above under 1 to 7 make improvements in the production of OLEDs necessary.

A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, *Appl. Phys. Lett.* 1999, 75, 4-6]. For quantum-mechanical reasons, up to four times the quantum efficiency, energy efficiency and power efficiency are possible using organometallic compounds. Whether this new development will establish itself firstly depends strongly upon whether corresponding device compositions can be found which can also utilize these advantages (triplet emission=phosphorescence compared to singlet emission=fluorescence) in OLEDS. The essential conditions for practical use here are in particular a high operative lifetime, a high stability against thermal stress and a low use and operating voltage in order to enable mobile applications.

The general structure of organic electroluminescent devices is described, for example, in U.S. Pat. No. 4,539,507 and U.S. Pat. No. 5,151,629, and also EP 01202358.

Typically, an organic electroluminescent device consists of a plurality of layers which are applied by means of vacuum methods or various printing methods. These layers are specifically:

1. a carrier plate=substrate (typically glass or plastics films).
2. A transparent anode (typically indium tin oxide, ITO).
3. A hole injection layer (Hole Injection Layer=HIL): for example based on copper-phthalocyanine (CuPc) or conductive polymers such as polyaniline (PANI) or polythiophene derivatives (such as PEDOT).
4. One or more hole transport layers (Hole Transport Layer=HTL): typically based on triarylamine derivatives, for example 4,4',4"-tris(N-1-naphthyl-N-phenylamino) triphenylamine (NaphDATA) as the first layer and N,N'-di(naphth-1-yl)-N,N'-diphenylbenzidine (NPB) as the second hole transport layer.
5. One or more emission layers (Emission Layer=EML): this layer (or layers) may coincide partly with layers 4 to 8, but consists typically of matrix materials, such as 4,4'-bis (carbazol-9-yl)biphenyl (CBP), doped with fluorescent dyes, for example N,N'-diphenylquinacridone (QA), or phosphorescence dyes, for example tris(2-phenylpyridyl) iridium (Ir(PPy)$_3$) or tris(2-benzothiophenylpyridyl)iridium (Ir(BTP)$_3$). However, the emission layer may also consist of polymers, mixtures of polymers, mixtures of polymers and low molecular weight compounds or mixtures of different low molecular weight compounds.
6. A hole-blocking layer (Hole-Blocking Layer=HBL): this layer may coincide partly with layers 7 and 8. It consists typically of BCP (2,9-dimethyl-4,7-diphenyl-1,10-phenanthroline=bathocuproin) or bis(2-methyl-8-quinolinolato)(4-phenylphenolato)aluminum(III) (BAlq).
7. An electron transport layer (Electron Transport Layer=ETL): usually based on aluminum tris-8-hydroxyquinolate (AlQ$_3$).
8. An electron injection layer (Electron Injection Layer=EIL): this layer may coincide partly with layer 4, 5, 6 and 7, or a small portion of the cathode is specially treated or specially deposited.
9. A further electron injection layer (Electron Injection Layer=EIL): a thin layer consisting of a material having a high dielectric constant, for example LiF, Li$_2$O, BaF$_2$, MgO, NaF.
10. A cathode: here, generally metals, metal combinations or metal alloys having a low work function are used, for example Ca, Ba, Cs, Mg, Al, In, Mg/Ag.

This whole device is appropriately (depending on the application) structured, contacted and finally also hermetically sealed, since the lifetime of such devices is generally shortened drastically in the presence of water and/or air. The same also applies to what are known as inverted structures in which the light is emitted from the cathode. In these inverted OLEDs, the anode consists, for example, of Al/Ni/NiOx or Al/Pt/PtOx or other metal/metal oxide combinations which have a HOMO greater than 5 eV. The cathode consists of the same materials as described in point 9 and 10, with the difference that the metal, for example Ca, Ba, Mg, Al, In, etc, is very thin and thus transparent. The layer thickness is below 50 nm, better below 30 nm, even better below 10 nm. A further transparent material can also be applied to this transparent cathode, for example ITO (indium tin oxide), IZO (indium zinc oxide), etc.

In the abovementioned structure, the matrix material of the emission layer (EML) plays a particular role. The matrix material has to enable or improve the charge transport of holes and/or electrons, and/or enable or improve charge carrier recombination, and, if appropriate, transfer the energy arising in the recombination to the emitter. In the electroluminescent devices based on phosphorescent emitters, this task has to date been assumed predominantly by matrix materials which contain carbazole units.

However, matrix materials which contain carbazole units, for example the frequently used 4,4'-bis(N-carbazolyl)biphenyl (CBP), have some disadvantages in practice. These can be seen, inter alia, in the often short to very short lifetime of the devices produced with them and the frequently high operating voltages which lead to low power efficiencies. In addition, it has been found that, for energetic reasons, CBP is unsuitable for blue-emitting electroluminescent devices, which results in a very poor efficiency. Moreover, the structure of the devices is very complex when CBP is used as the matrix material, since a hole blocking layer and an electron transport layer have to be used in addition. When these additional layers are not used, as described, for example, by Adachi et al. (*Organic Electronics* 2001, 2, 37) good efficiencies are observed but only at extremely low brightnesses, while the efficiency at higher brightness, as required for application, is lower by more than one order of magnitude. Thus, high voltages are required for high brightnesses, so that the power efficiency is very low here, which is unsuitable especially for passive matrix applications.

It has now been found that, surprisingly, the use of certain matrix materials in combination with certain emitters leads to distinct improvements over the prior art, especially in relation to the efficiency and in combination with a greatly increased lifetime. In addition, a distinctly simplified layer structure of the OLEDs is possible with these matrix materials, since neither a separate hole blocking layer nor a separate electron transport and/or electron injection layer has to be used. This is an enormous technological advantage.

Figure 1:
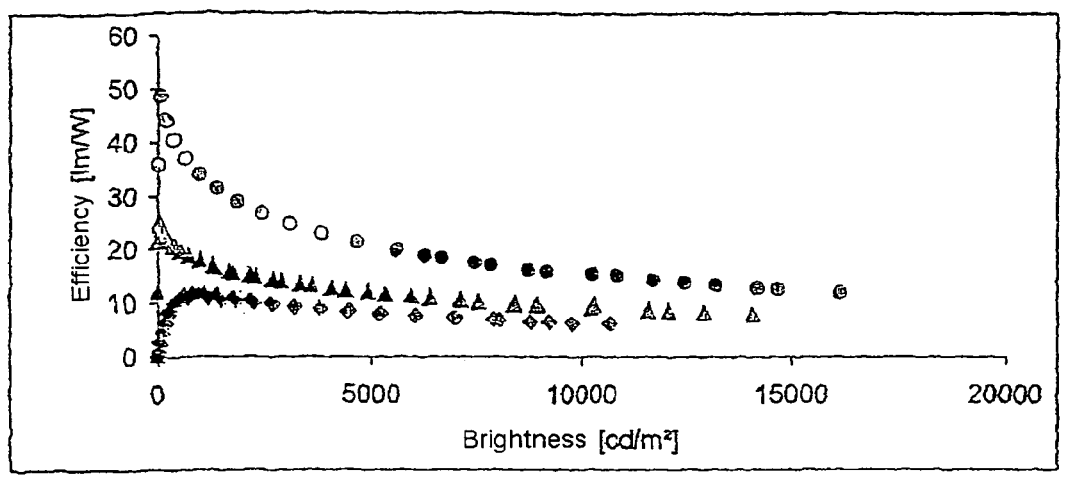
FIG. 1 illustrates the power efficiency versus the brightness.

The use of the matrix materials described below in OLEDs which comprise phosphorescent emitters is just as novel as the underlying mixture. The use of analogous materials in simple devices, as emission materials themselves or as materials in the emission layer in combination with fluorescent emitters, has already been described in occasional references in the literature (e.g.: JP 06192654). There is likewise a description (WO 04/013080) of aroyl derivatives of spirobifluorene which can also be used in OLEDs, but without reference to triplet emission, electrophosphorescence or matrix materials therefor; this can thus be evaluated as a coincidental disclosure. The novelty of the invention described below is not prejudiced by the abovementioned descriptions, since the use of the matrix materials described below in OLEDs in combination with phosphorescent emitters is novel.

The invention therefore provides mixtures comprising
  at least one matrix material A which contains a structural unit of the form C=Q in which Q has at least one nonbonding electron pair and represents the element O, S, Se or N, and which can in some cases also form glasslike layers, and
  at least one emission material B which is capable of emission and is a compound which, upon suitable excitation, emits light, and contains at least one element of atomic number greater than 20.

The inventive mixtures are preferably those which comprise at least one matrix material A for which the glass transition temperature $T_g$ of the pure substance A is greater than 70° C., preferably greater than 100° C., more preferably greater than 130° C.

The matrix material A present in the above-described mixtures is preferably at least one compound of the formula (1), formula (2) and/or formula (3)

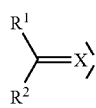

formula (1)

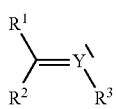

formula (2)

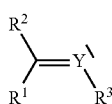

formula (3)

where the symbols and indices are each defined as follows:
X is the same or different at each instance and is O, S or Se;
Y at each instance is N;
$R^1$, $R^2$, $R^3$ is the same or different at each instance and is H, CN, a straight-chain, branched or cyclic alkyl, alkoxy or alkylamino group having from 1 to 40 carbon atoms, in which one or more nonadjacent $CH_2$ groups may be replaced by —$R^4C$=$CR^4$—, —C≡C—, C=O, C=S, C=Se, C=$NR^4$, —O—, —S—, —$NR^5$— or —$CONR^6$—, and in which one or more hydrogen atoms may be replaced by F, Cl, Br, I, or an aromatic or heteroaromatic system having from 1 to 40 carbon atoms, in which one or more hydrogen atoms may be replaced by F, Cl, Br, I, and which may be substituted by one or more nonaromatic $R^1$ radicals, and a plurality of substituents $R^1$ and/or $R^1$, $R^2$, either on the same ring or on the two different rings, may together in turn form a further mono- or polycyclic, aliphatic or aromatic ring system; with the proviso that $R^1$=$R^2$=$R^3$≠hydrogen;
$R^4$, $R^5$, $R^6$ are the same or different at each instance and are H or an aliphatic or aromatic hydrocarbon radical having from 1 to 20 carbon atoms.

In the context of this invention, an aromatic or heteroaromatic system shall be understood to mean a system which does not necessarily contain only aromatic or heteroaromatic groups, but in which a plurality of aromatic or heteroaromatic groups may also be interrupted by a short nonaromatic unit (<10% of the atoms, preferably <5% of the atoms), for example sp³-hybridized C, O, N, etc. For example, aromatic systems should thus also be understood to mean systems such as 9,9'-spirobifluorene, 9,9-diarylfluorene, triarylamine, diphenyl ether, etc.

Even if this is evident from the definition above, it is explicitly pointed out here once again that the $R^1$ or $R^2$ radical may also be a substituted or unsubstituted vinyl group or a corresponding derivative, i.e. that the compound of the formula (1) may also be an α,β-unsaturated carbonyl compound, or the compound of the formula (2) or (3) may also be an α,β-unsaturated imine.

Particularly suitable compounds of the formula (1) to (3) have been found to be compounds which do not have a planar structure. On the structural unit of the form C=Q, appropriate substituents can ensure deviation of the overall structure from planarity. This is the case especially when at least one of the substituents $R^1$, $R^2$ and/or $R^3$ contains at least one sp³-hybridized carbon, silicon, germanium and/or nitrogen atom, which thus has approximately tetrahedral, or, in the case of nitrogen, pyramidal bonding geometry.

In order to achieve a distinct deviation from planarity, it is preferred when at least one of the sp³-hybridized atoms is a secondary, tertiary or quaternary atom, more preferably a tertiary or quaternary atom, in the case of carbon, silicon or germanium most preferably a quaternary atom.

A secondary, tertiary or quaternary atom is understood respectively to mean an atom having two, three or four substituents other than hydrogen.

Preference is further given to compounds which, in at least one of the $R^1$ to $R^3$ radicals, contain a 9,9'-spirobifluorene derivative, preferably bonded via the 2- and/or 2,7- and/or 2,2'- and/or 2,2',7- and/or 2,2',7,7'-position, a 9,9-disubstituted fluorene derivative, preferably bonded via the 2- and/or 2,7-position, a 6,6- and/or 12,12-di- or tetrasubstituted indenofluorene derivative, a triptycene derivative, preferably bonded via the 9- and/or 10-position, a dihydrophenanthrene derivative, preferably bonded via the 2- and/or 2,7- and/or 3- and/or 3,6-position, or a hexaarylbenzene derivative, preferably bonded via the p-position, to the aromatic(s).

Particular preference is given to compounds which contain a 9,9'-spirobifluorene derivative in at least one of the $R^1$ to $R^3$ radicals.

Preference is once again further given to compounds which contain a substituted or unsubstituted 2-biphenyl or a substituted or unsubstituted 2-biphenyl ether in at least one of the $R^1$ to $R^3$ radicals.

Preference is further given to compounds which have a dendritic structure. Preference is also given to 1,3,5-trisubstituted benzene ketones and corresponding oligo ketones which are obtainable, for example, according to N. Nakamura et al., *J. Amer. Chem. Soc.* 1992, 114, 1484, or according to K. Matsuda et al., *J. Amer. Chem. Soc.* 1995, 177, 5550.

In order to avoid misunderstanding, it is emphasized at this point that matrix materials A with the structural unit C=Q of course do not mean aromatic systems which contain partial C=N double bonds in the ring, for example pyrimidines, pyrazines, etc.

Preference is likewise given to mixtures which comprise, as a matrix material A, at least one compound of the formula (4) to (9)

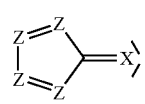

formula (4)

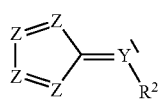

formula (5)

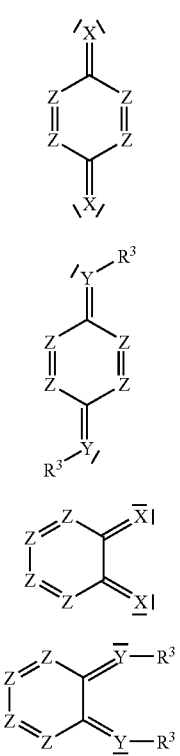

where the symbols X, Y, $R^1$, $R^2$, $R^3$ $R^4$, $R^5$ and $R^6$ are each as defined under formulae (1) to (3) and Z is the same or different at each instance and is $CR^1$ or N.

Particular preference is given to organic mixtures which contain at least one of the matrix materials A described above by formula (1) to (9) in which:

X at each instance is O or S;

Y at each instance is N;

Z at each instance is $CR^1$;

$R^1$, $R^2$, $R^3$ is the same or different at each instance and is H, a straight-chain, branched or cyclic alkyl group which has from 1 to 40 carbon atoms and preferably no hydrogen atoms in the α-position to the keto or imine function, in which one or more nonadjacent $CH_2$ groups may be replaced by $—R^4C=CR^4—$, $—C\equiv C—$, $C=O$, $C=S$, $C=Se$, $C=NR^4$, $—O—$, $—S—$, $—NR^5—$ or $—CONR^6—$, and in which one or more hydrogen atoms may be replaced by F, Cl, Br, I, or an aromatic or heteroaromatic system having from 1 to 40 carbon atoms, in which one or more hydrogen atoms may be replaced by F, Cl, Br, I, and which may be substituted by one or more nonaromatic $R^1$ radicals, and a plurality of substituents $R^1$ and/or $R^1$, $R^2$, either on the same ring or on the different rings, may together in turn form a further mono- or polycyclic, aliphatic or aromatic ring system, $R^4$, $R^5$, $R^6$ are each as described under formula (1) to (3).

Preference is likewise given to mixtures which contain, as a matrix material A, at least one compound of the formula (10) to (15)

Where the symbols Z, Y and $R^1$ to $R^6$ are each defined as described under formula (1) to (9), and the further symbols and indices are:

Ar is the same or different at each instance and is an aromatic or heteroaromatic system having from 2 to 40 carbon atoms, preferably having from 4 to 30 carbon atoms, in which one or more hydrogen atoms may be replaced by F, Cl, Br, I, and which may be substituted by one or more nonaromatic $R^1$ radicals, and a plurality of substituents $R^1$, either on the same ring or on different rings, may together in turn form a further mono- or polycyclic, aliphatic or aromatic ring system;

n is the same or different at each instance and is 0 or 1.

The reason for the preference for these materials of the formula (10) to (15) is in particular their high glass transition temperatures. Depending on the substitution pattern, these are typically above 70° C. and usually above 100° C.

The present invention likewise provides the novel compounds of the formula (10a) to (15)

formula (10a)

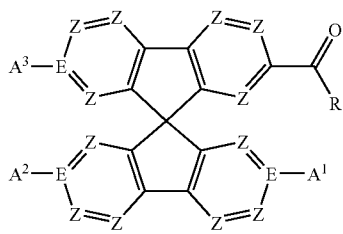

formula (11)

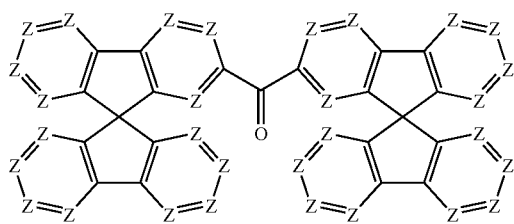

formula (12)

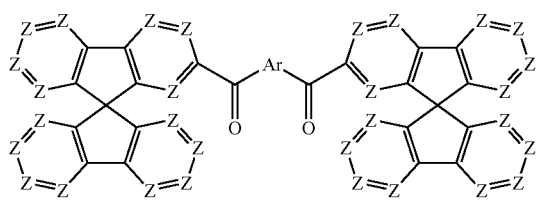

formula (13)

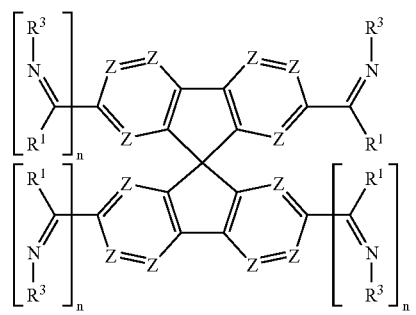

-continued formula (14)

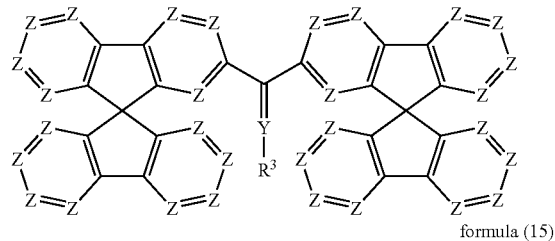

formula (15)

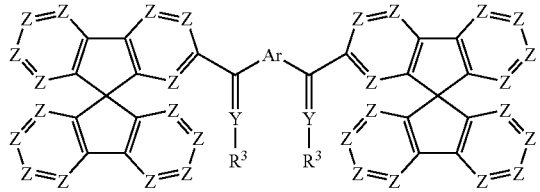

in which the symbols Z, Y, Ar and $R^1$ to $R^6$ are each as defined above, and the further symbols used are:

E is the same or different at each instance is C or N;

$R^7$ is the same or different at each instance and is an alkyl, alkoxy or alkylamino group having from 1 to 40 carbon atoms, in which one or more $CH_2$ groups may also be replaced by $-R^4C=CR^4-$, $-C\equiv C-$, C=O, C=S, C=Se, $C=NR^4$, $-O-$, $-S-$, $-NR^4$ or $-CONR^4-$, and in which one or more hydrogen atoms may also be replaced by F, Cl, Br, I, with the proviso that no hydrogen atoms are bonded in the α-position to the carbonyl group, or an aromatic group which may optionally be substituted by halogen, alkyl, trifluoromethyl, hydroxyl, —SH, —S-alkyl, alkoxy, nitro, cyano, —COOH, —COoalkyl, —$NH_2$, —Nalkyl, benzyl or benzoyl, or a larger aromatic system having from 2 to 40 carbon atoms, preferably from 4 to 30 carbon atoms, for example 9,9'-spirobifluorene, fluorene, triarylamine, etc., in which one or more hydrogen atoms may be replaced by F, Cl, Br, I, and which may be substituted by one or more nonaromatic $R^1$ radicals, and a plurality of substituents $R^1$ may in turn form a further mono- or polycyclic, aliphatic or aromatic ring system;

$A^1$ at each instance is $R^8$ or CO—$R^7$ when X=C or is a free electron pair when X=N;

$A^2$ at each instance is $R^8$ or CO—$R^7$ when X=C or is a free electron pair when X=N;

$A^3$ at each instance is $R^8$ or CO—$R^7$ when X=C or is a free electron pair when X=N;

$R^8$ is the same or different at each instance and is H, F, Cl, Br, I, CN, $NO_2$, a straight-chain or branched or cyclic alkyl group having from 1 to 40 carbon atoms, in which one or more nonadjacent $CH_2$ groups may be replaced by $-R^4C=CR^4-$, $-C\equiv C-$, C=S, C=Se, $C=NR^4$, $-O-$, $-S-$, $-NR^4$ or $-CONR^4-$, and in which one or more hydrogen atoms may be replaced by F, Cl, Br, I, or an aromatic or heteroaromatic system having from 1 to 40 carbon atoms, in which one or more hydrogen atoms may be replaced by F, Cl, Br, I, and which may be substituted by one or more nonaromatic $R^1$ radicals, and a plurality of substituents $R^1$ and/or $R^1/R^4$, either on the same ring or on the different rings, may together in turn form a further mono- or polycyclic, aliphatic or aromatic ring system;

with the proviso that, for the compound of the formula (10a), only the following combinations are permitted for the symbols described, where $R^8$ and $R^4$ can be selected freely according to the definition:

group other than H, the symbol $A^3$ is a CO—$R^7$ group where $R^7$ here can be selected freely according to the definition;

when $R^7$ is a larger aromatic system, for example fluorene, spirobifluorene, triarylamine, etc., the symbols Z, E, $A^1$, $A^2$ and $A^3$ can be selected freely according to the definition.

For the sake of clarity, the permitted combinations of the symbols $R^7$, Z, E, $A^1$, $A^2$ and $A^3$ for compounds of the formula (10a) are compiled in table 1.

TABLE 1

Possible combinations of the symbols $R^7$, Z, E, $A^1$, $A^2$ and $A^3$ for compounds of the formula (10a).

| $R^7$ | Z | E | $A^1$ | $A^2$ | $A^3$ |
|---|---|---|---|---|---|
| alkyl without α-H | any according to the definition | any according to the definition | any according to the definition | any according to the definition | any according to the definition |
| aromatic group | at least 1 Z = N | any according to the definition | any according to the definition | any according to the definition | any according to the definition |
| aromatic group | at least 1 Z = $CR^1$ where at least 1 $R^1$ is not H | any according to the definition | any according to the definition | any according to the definition | any according to the definition |
| aromatic group | all Z = CH | at least 1 E = N | any according to the definition | any according to the definition | any according to the definition |
| aromatic group | all Z = CH | All E = C | $R^8$ is not alkyl | any according to the definition | any according to the definition |
| aromatic group | all Z = CH | all E = C | any according to the definition | $R^8$ is not alkyl | any according to the definition |
| aromatic group | all Z = CH | all E = C | any according to the definition | any according to the definition | $R^8$ is not alkyl |
| aromatic group | all Z = CH | all E = C | any according to the definition, is not H | any according to the definition | CO—$R^7$ ($R^7$ according to the definition) |
| aromatic group | all Z = CH | all E = C | any according to the definition | any according to the definition, is not H | CO—$R^7$ ($R^7$ according to the definition) |
| larger aromatic system (e.g. fluorene, spirobifluorene, . . . ) | any according to the definition | any according to the definition | any according to the definition | any according to the definition | any according to the definition | when $R^7$ is an alkyl group without α-hydrogen atoms, the symbols Z, E, $A^1$, $A^2$ and $A^3$ can be selected freely according to the definition;

when $R^7$ is an aromatic group and at least one Z is N, the symbols E, $A^1$, $A^2$ and $A^3$ can be selected freely according to the definition;

when $R^7$ is an aromatic group and at least one Z is a $CR^1$ group where $R^1$ is other than H, the symbols E, $A^1$, $A^2$ and $A^3$ can be selected freely according to the definition;

when $R^7$ is an aromatic group and all Z are CH and at least one symbol E is N, the symbols $A^1$, $A^2$ and $A^3$ can be selected freely according to the definition;

when $R^7$ is an aromatic group, all Z are CH and all E are C, at least one of the symbols $A^1$, $A^2$ and/or $A^3$ has to be an $R^8$ group other than alkyl, while the two other groups can be selected freely according to the definition;

when $R^7$ is an aromatic group, all Z are CH, all E are C and the two symbols $A^1$ and $A^2$ are selected freely according to the definition, at least one of the two symbols being a Preference is given to compounds in which at least one R7 group describes a larger aromatic system, for example fluorene, spirobifluorene, arylamine, etc.

Preference is further given to compounds in which at least one $R^7$ group is an alkyl group as defined above without α-hydrogen atoms.

Preference is further given to compounds in which at least one of the symbols A, B and/or D is an aromatic or heteroaromatic system.

Preference is further given to the compounds which contain more than one spirobifluorene unit.

Preference is further given to compounds in which at least one of the symbols Z or E is N.

Preference is further given to compounds which contain more than one keto function, i.e. diketones or oligoketones.

The present invention is illustrated in detail by the examples of matrix materials A which follow, without any intention to restrict it thereto. Those skilled in the art can prepare further matrix materials and use them in inventive mixtures from the description and the adduced examples without any inventive activity.

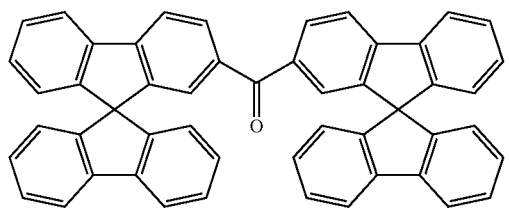
Example 1
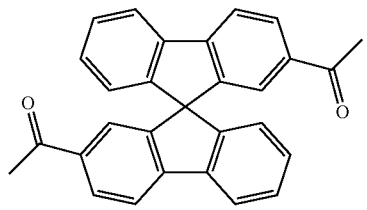
Example 2
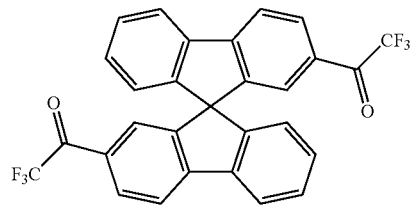
Example 3
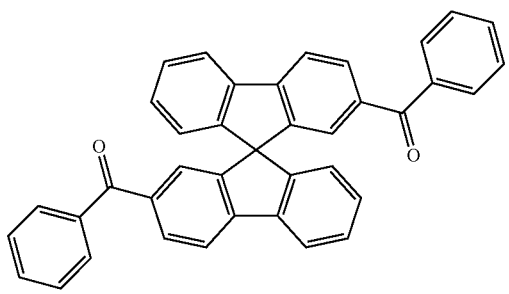
Example 4
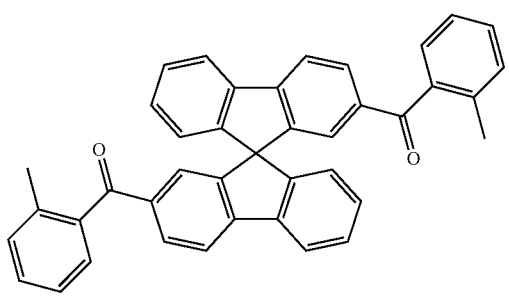
Example 5

-continued
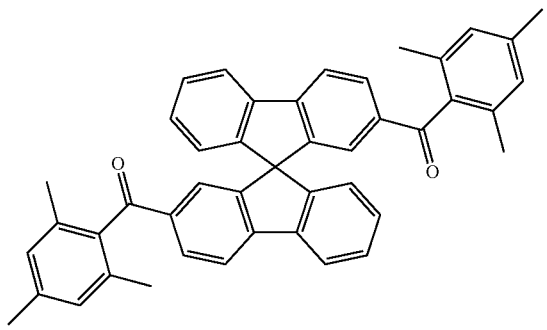
Example 6
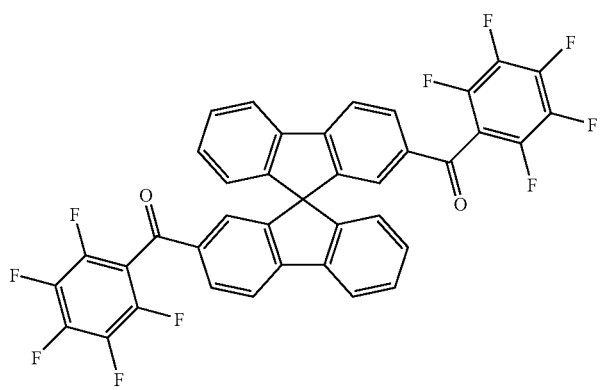
Example 7
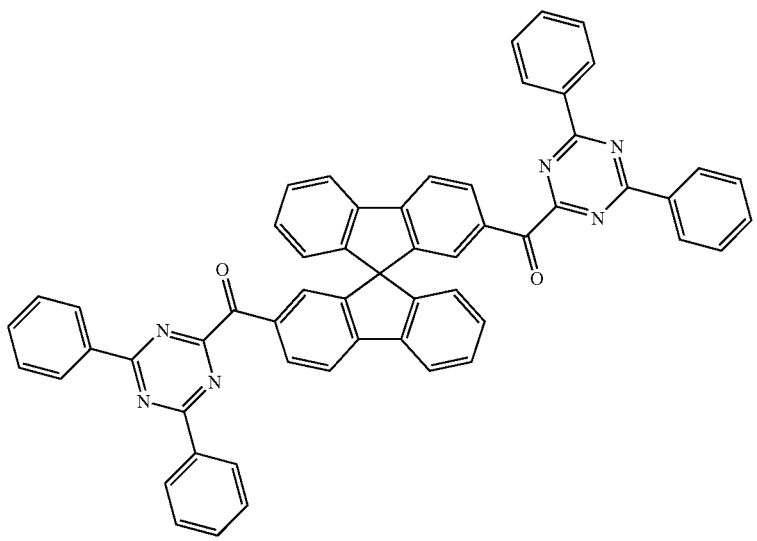
Example 8
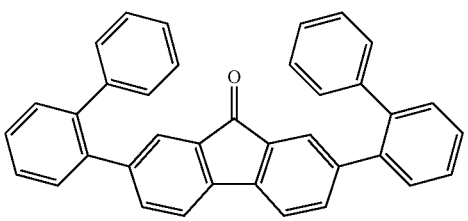
Example 9

-continued
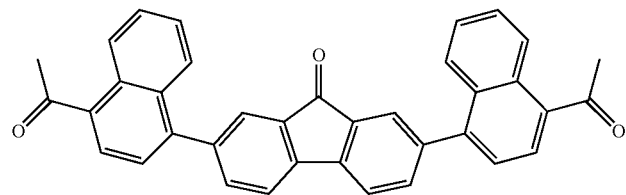
Example 10
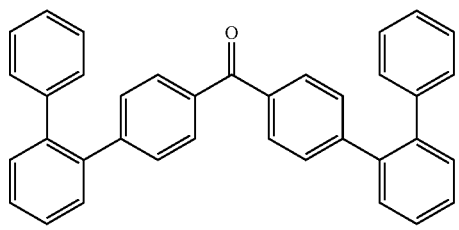
Example 11
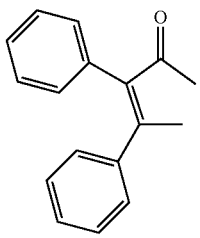
Example 12
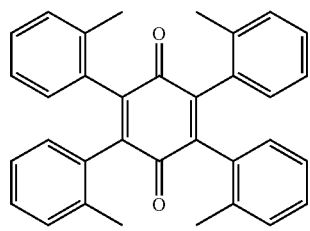
Example 13
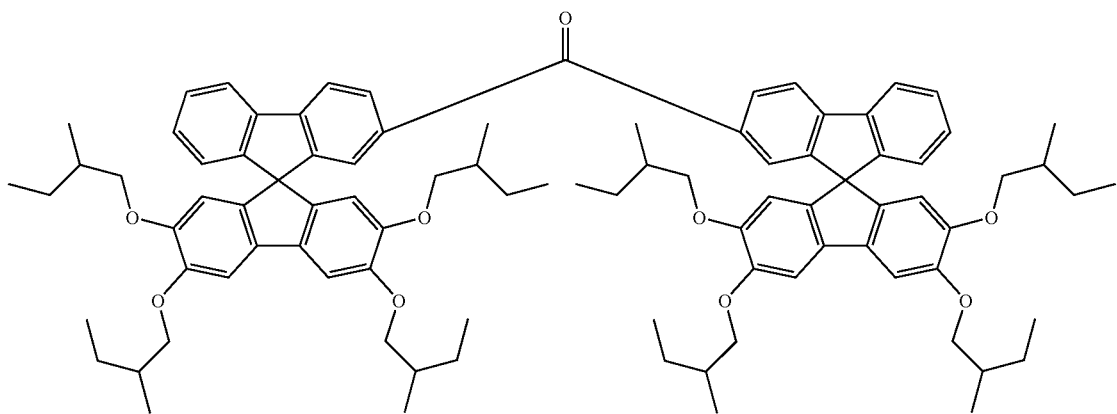
Example 14

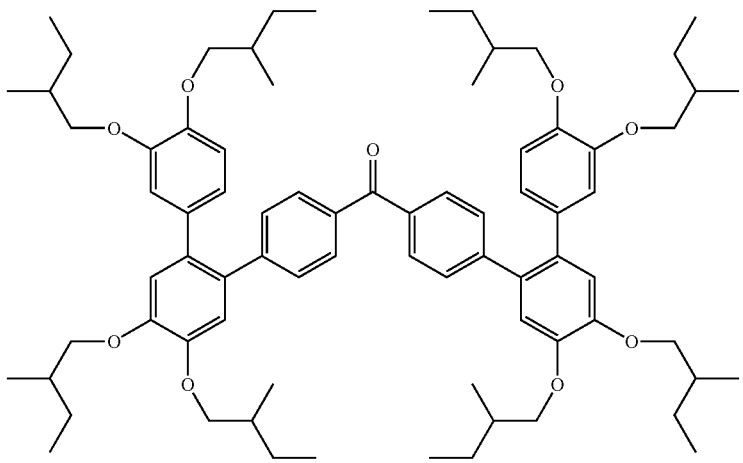
Example 15
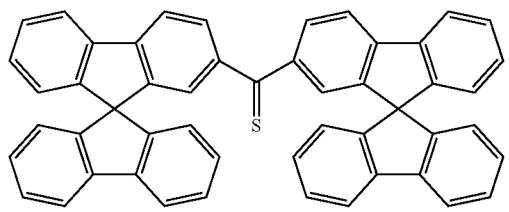
Example 16
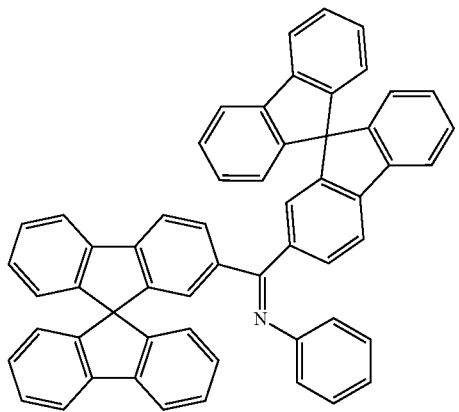
Example 17

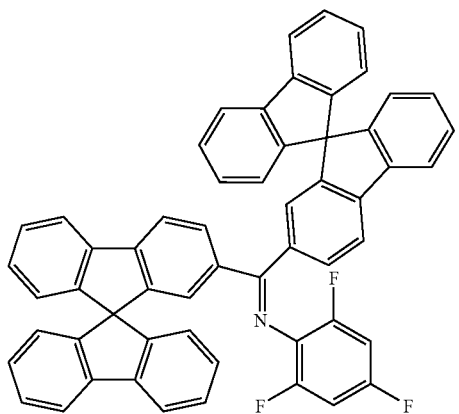
Example 18
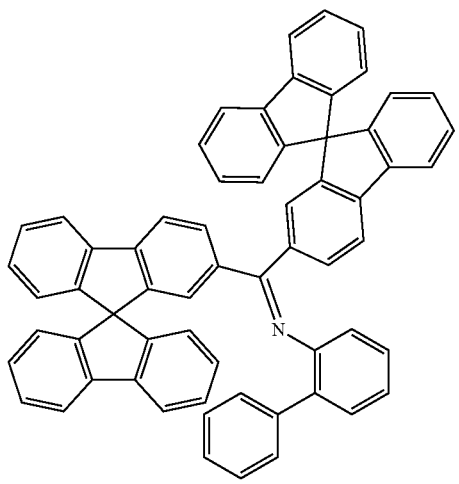
Example 19
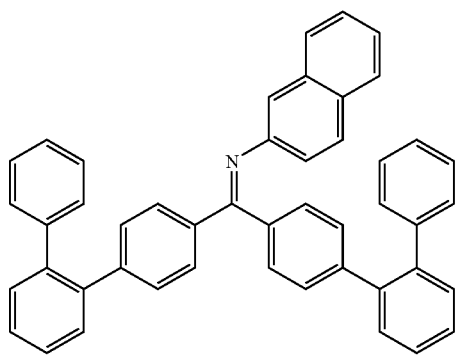
Example 20

-continued
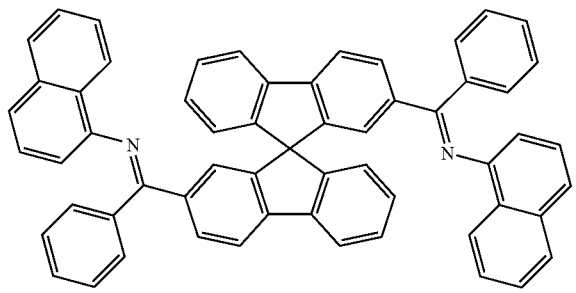
Example 21
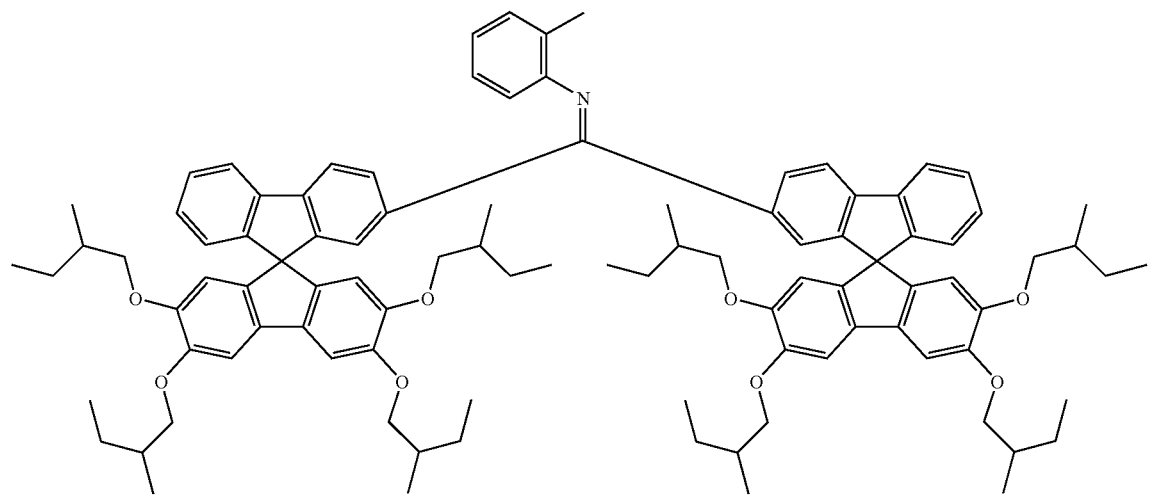
Example 22
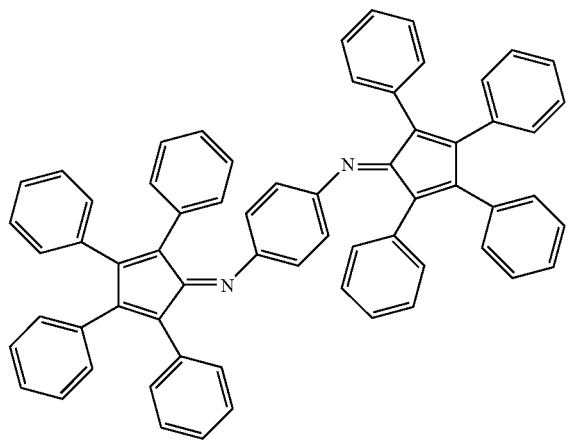
Example 23

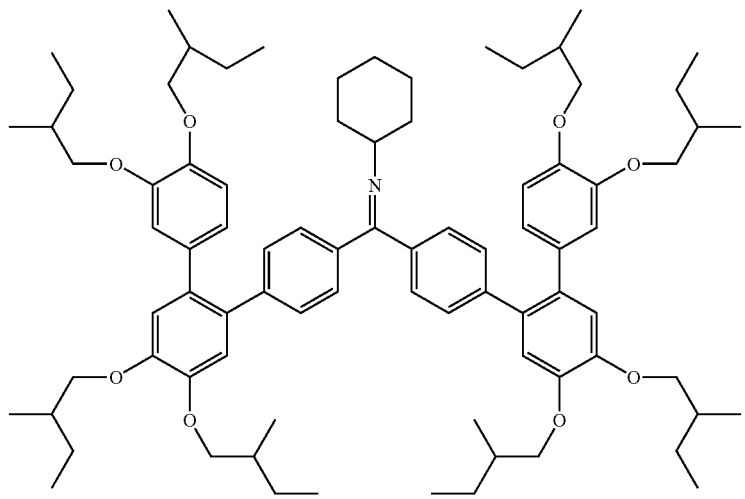
Example 24
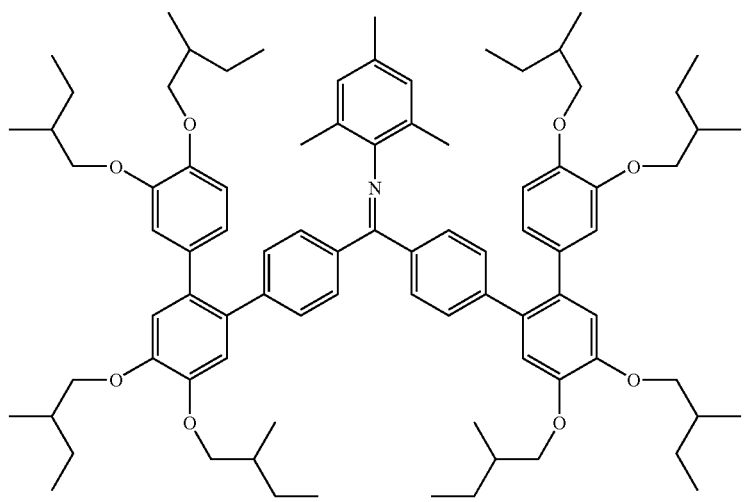
Example 25
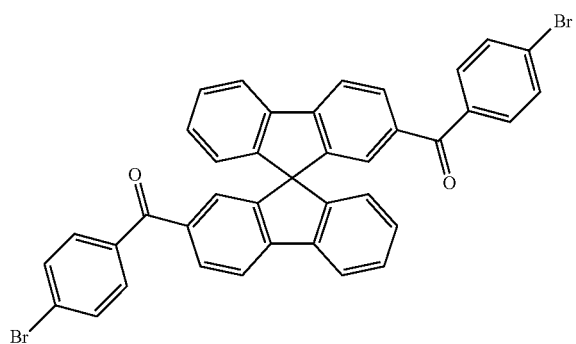
Example 26

-continued
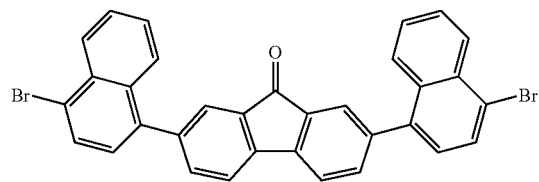
Example 27
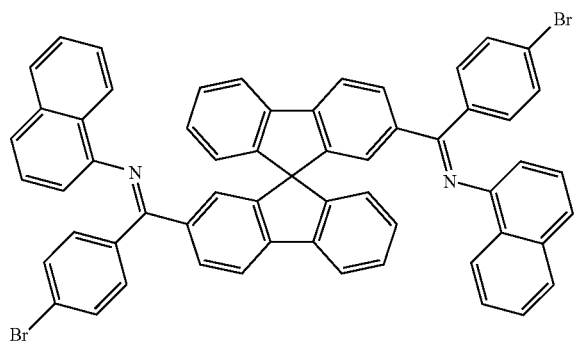
Example 28
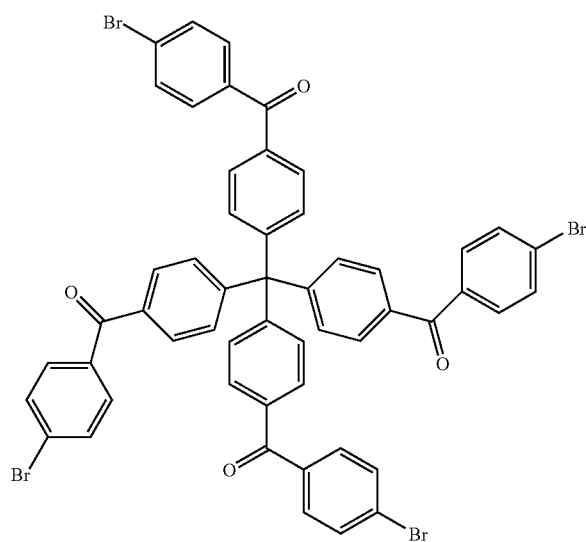
Example 29

-continued
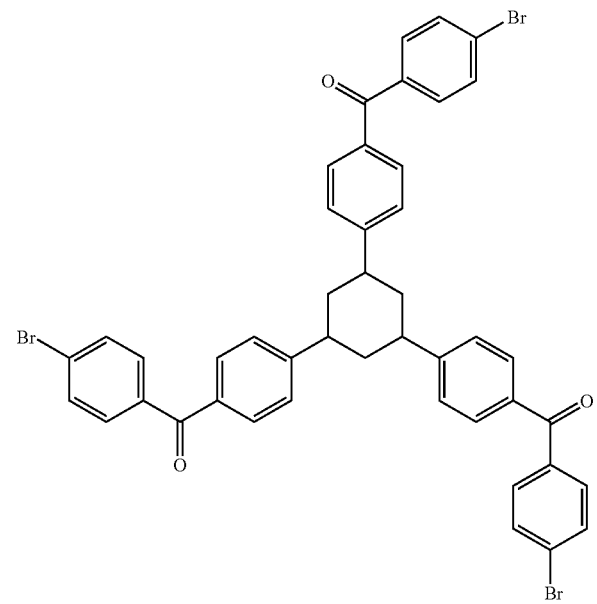
Example 30
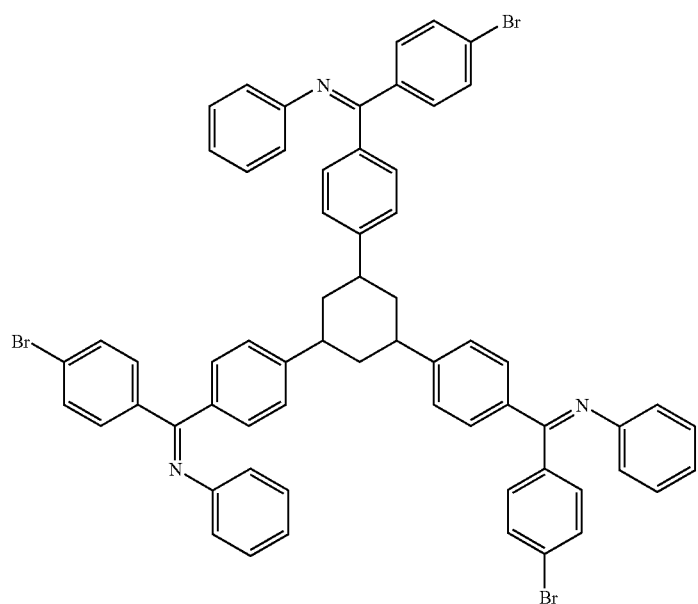
Example 31
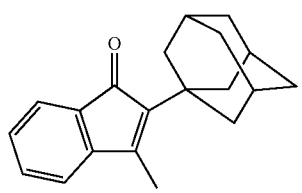
Example 32

-continued
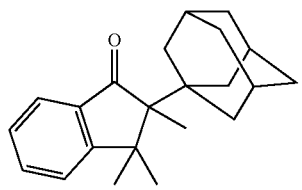
Example 33
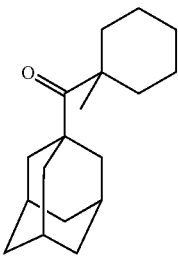
Example 34
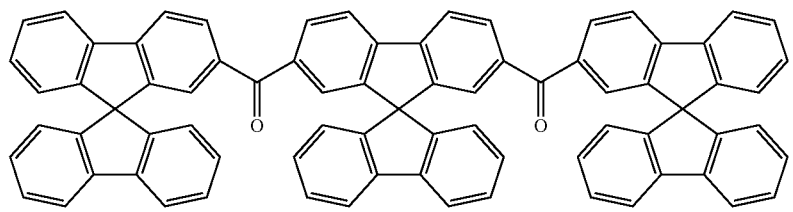
Example 35
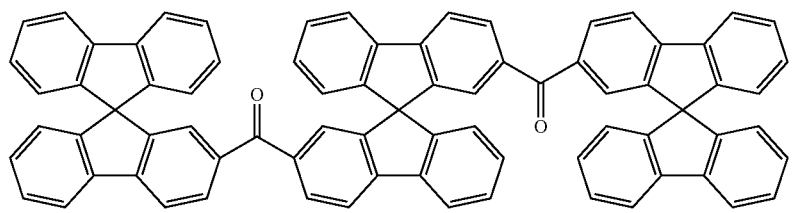
Example 36
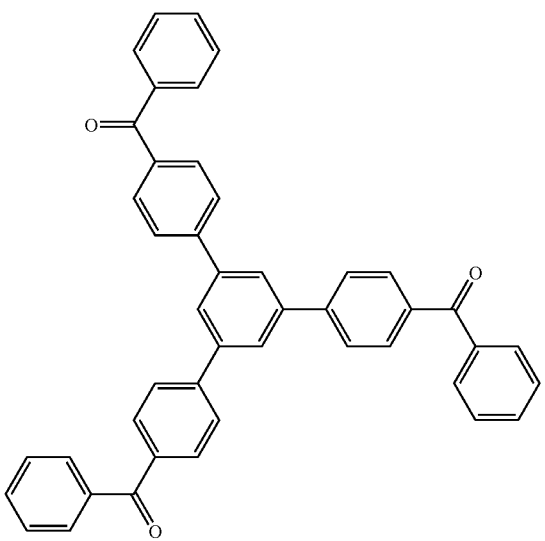
Example 37

-continued
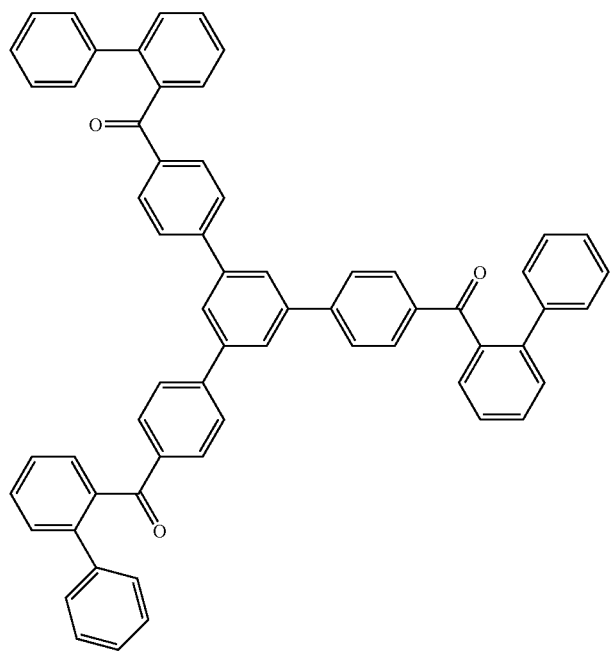
Example 38
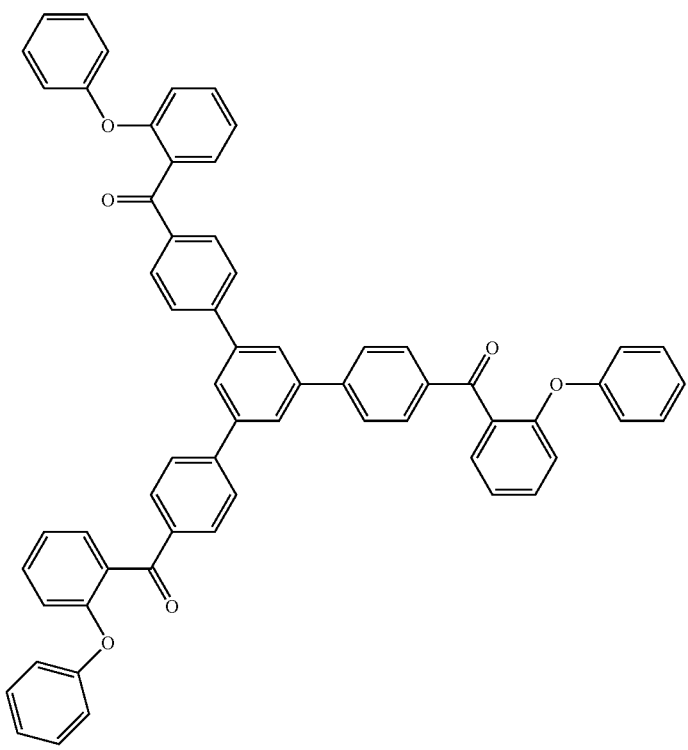
Example 39

-continued
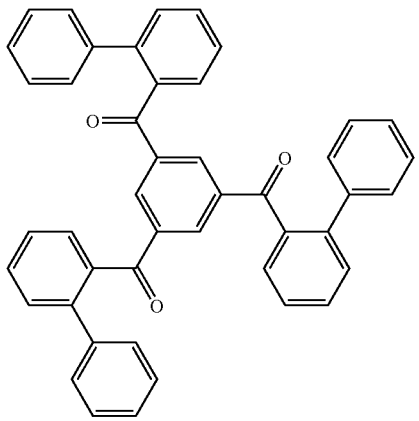
Example 40
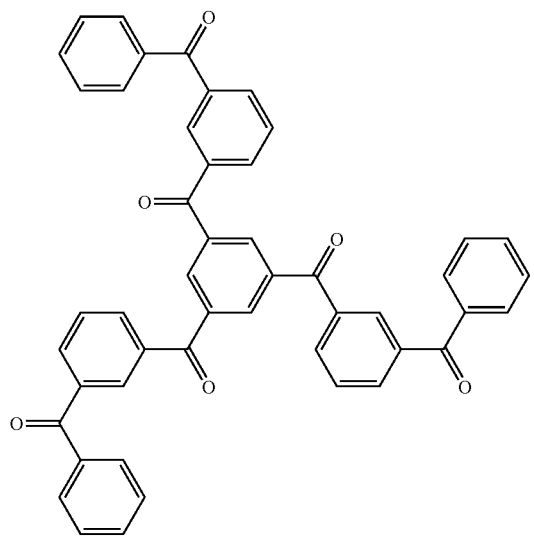
Example 41
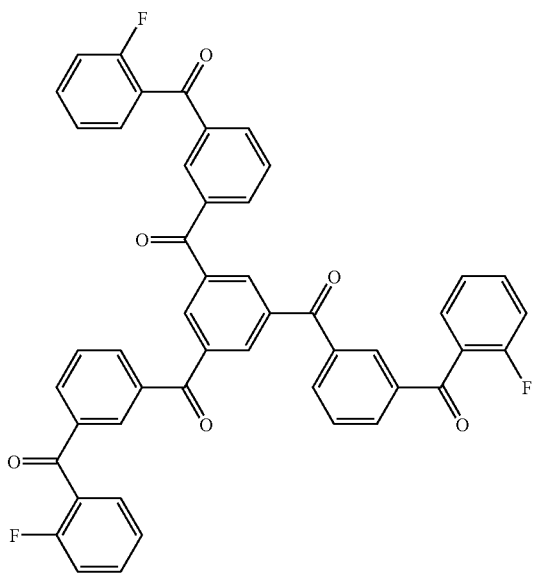
Example 42

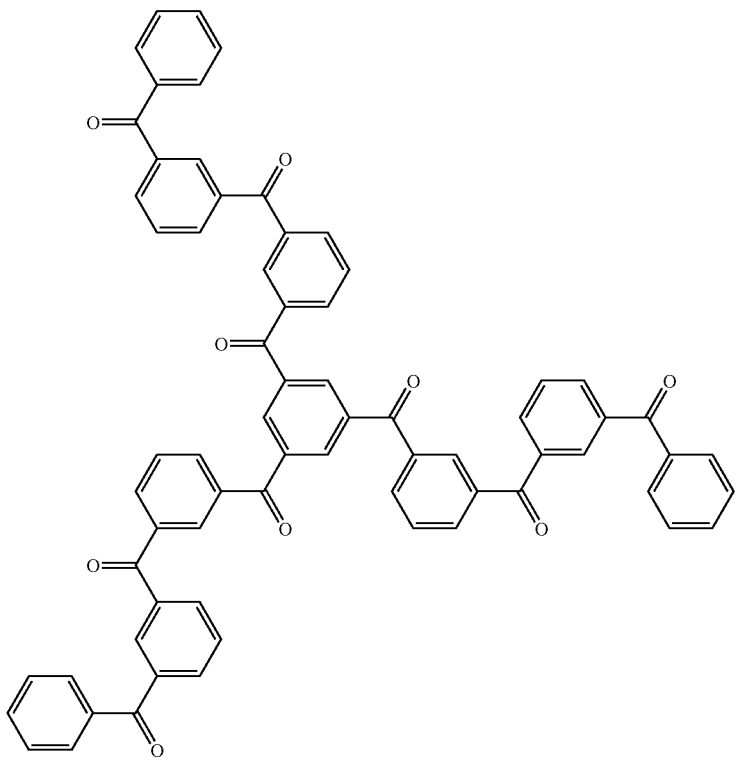
Example 43
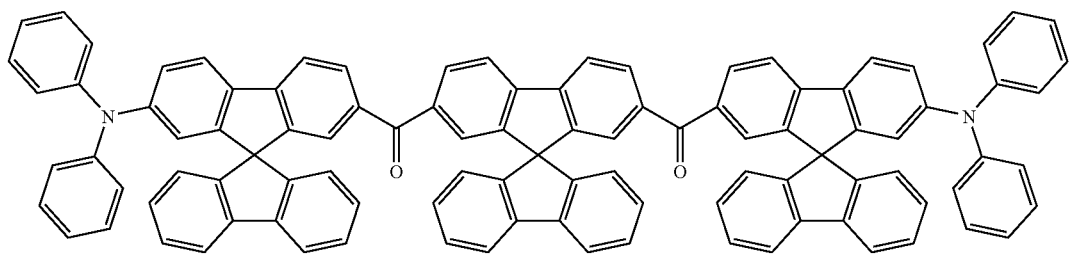
Example 44
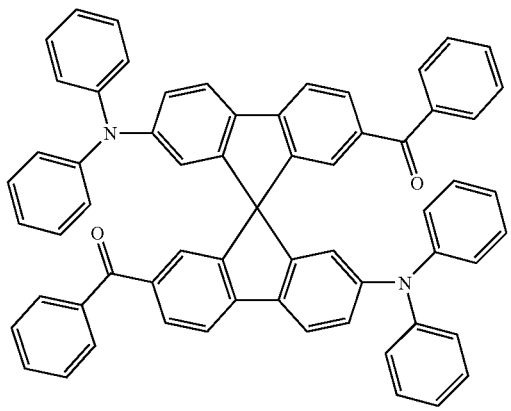
Example 45

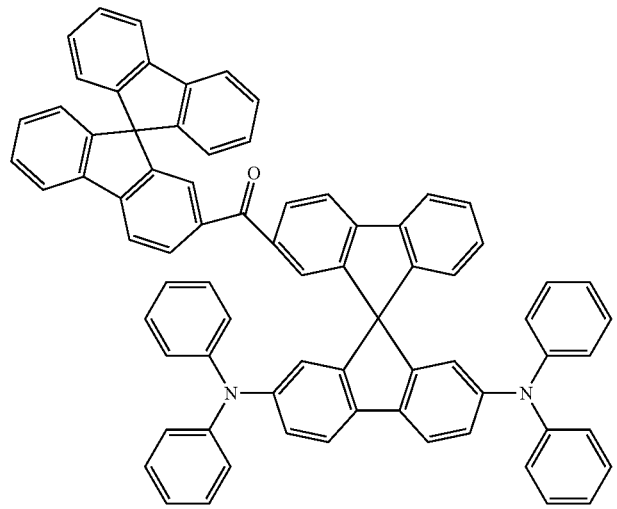
Example 46
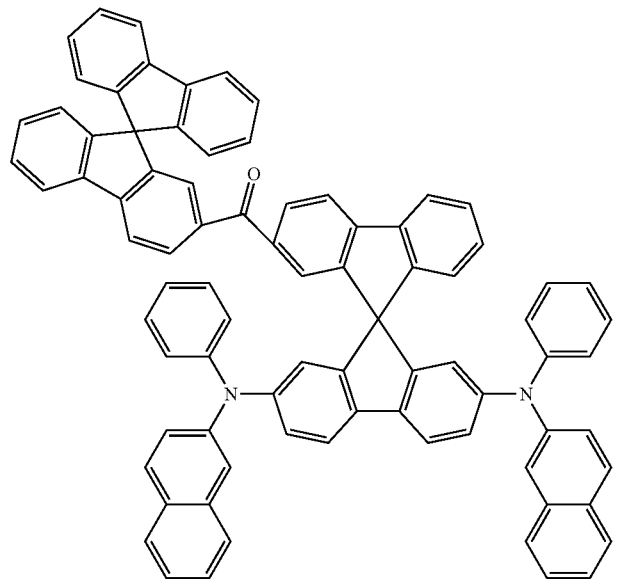
Example 47
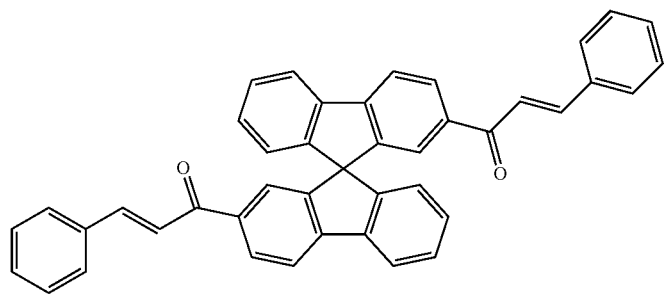
Example 48

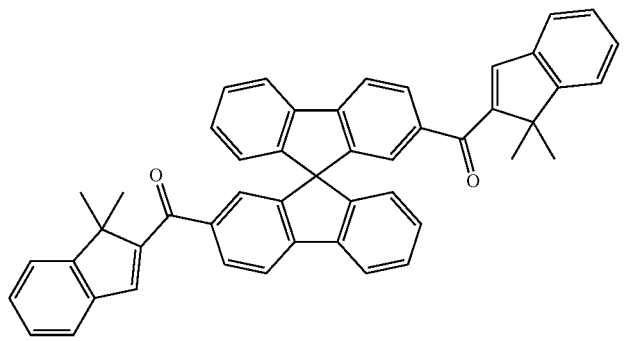

Example 49

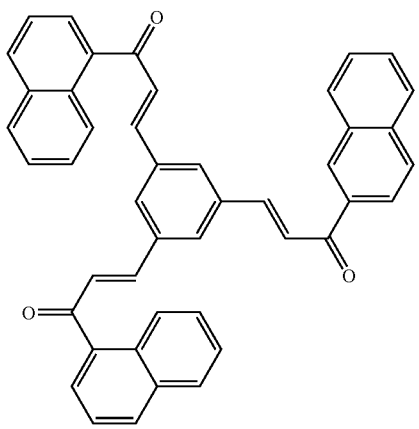

Example 50

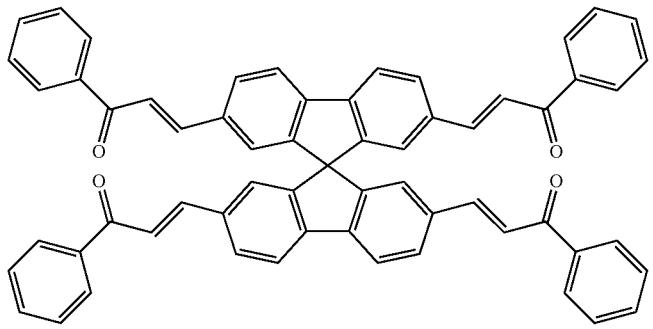

Example 51

The above-described matrix materials A, for example according to examples 26, 27 and 28, may also find use, for example, as comonomers for obtaining corresponding conjugated, semiconjugated or else nonconjugated polymers, or as the core of dendrimers, for example according to examples 29, 30 and 31. The corresponding polymerization is preferably effected via the halogen functionality.

For instance, they can be polymerized, inter alia, into soluble polyfluorenes (for example according to EP 842208 or WO 00/22026), poly-spirobifluorenes (for example according to EP 707020 or EP 894107), poly-para-phenylenes (for example according to WO 92/18552), polycarbazoles or else polythiophenes (for example according to EP 1028136).

The above-described conjugated, semiconjugated or non-conjugated polymers or dendrimers which contain one or more structural units of the formula (1) or (15) may be used as the matrix material in organic electroluminescent devices.

In addition, the inventive matrix materials A may also be functionalized further by, for example, the abovementioned reaction types, and thus converted to extended matrix materials A. Here, examples include the functionalization with arylboronic acids according to SUZUKI or with amines according to HARTWIG-BUCHWALD.

In order to find use as a functional materiel, the inventive matrix materials A or their mixtures or the polymers or dendrimers containing matrix materials A, if appropriate together with the emitters B, are applied to a substrate in the form of a film by commonly known methods familiar to those skilled in the art, such as vacuum evaporation, evaporation in a carrier gas stream or else from solution by spincoating, or by various printing processes (for example inkjet printing, offset printing, LITI printing, etc.).

The use of printing processes can have advantages with regard to the scalability of manufacture, and with regard to the adjustment of mixing ratios in blend layers used.

The above-described matrix materials are used in combination with phosphorescence emitters. These mixtures feature the presence, as an emitter B, of at least one compound, which is characterized in that it emits light upon suitable excitation and also contains at least one atom of atomic number greater than 20, preferably greater than 38 and less than 84, more preferably greater than 56 and less than 80.

The phosphorescence emitters used in the above-described mixtures are preferably compounds which contain molybdenum, tungsten, rhenium, ruthenium, osmium, rhodium, iridium, palladium, platinum, silver, gold or europium.

Particularly preferred mixtures comprise, as emitter B, at least one compound of the formula (16) to (19)

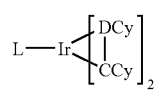

formula (16)

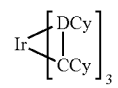

formula (17)

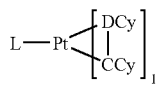

formula (18)

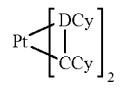

formula (19)

where the symbols used are:

DCy is the same or different at each instance and is a cyclic group which contains at least one donor atom, preferably nitrogen or phosphorus, via which the cyclic group is bonded to the metal atom, and which may in turn bear one or more substituents $R^9$; the DCy and CCy groups are joined together via a covalent bond;

CCy is the same or different at each instance and is a cyclic group which contains a carbon atom via which the cyclic group is bonded to the metal and which may in turn bear one or more substituents $R^9$;

$R^9$ is the same or different at each instance and is H, F, Cl, Br, I, $NO_2$, CN, a straight-chain or branched or cyclic alkyl or alkoxy group having from 1 to 40 carbon atoms, in which one or more nonadjacent $CH_2$ groups may be replaced by $-CR^4=CR^4-$, $-C\equiv C-$, $C=O$, $C=S$, $C=Se$, $C=NR^4$, $-O-$, $-S-$, $-NR^5-$ or $-CONR^6-$, and in which one or more hydrogen atoms may be replaced by F, or an aromatic or heteroaromatic system which has from 4 to 40 carbon atoms and may be substituted by one or more nonaromatic $R^9$ radicals; and a plurality of substituents $R^9$, either on the same ring or on the two different rings, may together in turn form a further mono- or polycyclic, aliphatic or aromatic ring system;

L is the same or different at each instance and is a bidentate chelating ligand, preferably a diketonate ligand;

$R^4$, $R^5$, $R^6$ is the same or different at each instance and is H or an aliphatic or aromatic hydrocarbon radical having from 1 to 20 carbon atoms.

Examples of the above-described emitters can be taken, for example, from the applications WO 00/70655, WO 01/41512, WO 02/02714, WO 02/15645, EP 1191613, EP 1191612, EP 1191614, WO 03/099959, WO 03/084972, WO 03/040160, WO 02/081488, WO 02/068435 and DE 10238903.9; these are hereby considered as part of the application by reference.

The inventive mixture contains between 1 to 99% by weight, preferably between 3 and 95% by weight, more preferably between 5 and 50% by weight, in particular between 7 and 20% by weight, of emitter B based on the overall mixture of emitter B and matrix material A.

The present invention further provides electronic components, in particular organic electroluminescent devices (OLEDs), organic solar cells (O-SCs), organic field-effect transistors (O-FETs) or else organic laser diodes (O-laser), comprising the inventive mixture of matrix material A and emission material B. Particular preference is given to organic electroluminescent devices which have an emitting layer (EML) comprising an inventive mixture of at least one matrix material A and at least one emission material B capable of emission.

Preference is given in particular to organic electroluminescent devices which contain, in the emitting layer (EML), at least one inventive mixture, the glass transition temperature $T_g$ of the pure substance of the matrix material A being greater than 70° C.

Apart from the cathode, the anode and the emitting layer, the organic electroluminescent device may comprise further layers, for example hole injection layer, hole transport layer, hole blocking layer, electron transport layer and/or electron injection layer. However, it should be pointed out here that not necessarily each of these layers need be present.

For example, it has been found that an OLED which contains neither a separate hole blocking layer nor a separate electron transport layer shows very good results in the electroluminescence, in particular a voltage which is once again distinctly lower and higher power efficiency. This is particularly surprising since a corresponding OLED with a carbazole-containing matrix material without hole blocking and electron transport layer exhibits only very low power efficiencies, especially at high brightness (cf. Adachi et al., *Organic Electronics* 2001, 2, 37). The invention thus further provides an organic electroluminescent device comprising an inventive mixture which, without use of a hole blocking layer, directly adjoins the electron transport layer, or which, without use of a hole blocking layer and of an electron transport layer, directly adjoins the electron injection layer or the cathode.

It has likewise been found that an OLED which does not contain any separate hole injection layer, but rather only one or more hole transport layers (triarylamine layers) directly on the anode likewise exhibits very good results in the electroluminescence. This structure thus also forms part of the subject matter of the present invention.

The inventive organic electroluminescent devices exhibit higher efficiency, distinctly longer lifetime and, especially without use of a hole blocking and electron transport layer, distinctly lower operating voltages and higher power efficiencies than prior art OLEDs which comprise CBP as the matrix material. Omission of the hole blocking and electron transport layers additionally distinctly simplifies the structure of the OLED, which constitutes a considerable technological advantage.

The preferred embodiments of the inventive mixtures of matrix material A and emission material B also apply to the inventive electronic components, in particular to the organic electroluminescent devices (OLEDs), organic solar cells (O-SCs), organic field-effect transistors (O-FETs) or else organic laser diodes (O-laser). To avoid unnecessary repetitions, another enumeration at this point is dispensed with.

In the present application text and also in the examples which follow, the aim is solely organic light-emitting diodes and the corresponding displays. In spite of this restriction of the description, it is possible for those skilled in the art without any further inventive activity to produce and employ corresponding inventive layers from the inventive mixtures, especially in OLED-like or related applications.

EXAMPLES

1. Synthesis of Matrix Materials A:

The syntheses which follow were, unless stated otherwise, carried out under a protective gas atmosphere in dried solvents. The reactants were purchased from ALDRICH [copper(I) cyanide, acetyl chloride, N-methylpyrrolidinone (NMP)]. 2-Bromo-9,9'-spirobifluorene, 2,7-dibromo-9,9'-spirobifluorene (J. Pei et al., *J. Org. Chem.* 2002, 67(14), 4924-4936) and 9,9'-spirobifluorene-2,2'-dicarbonyl chloride (V. A. Montero et al., *Tetrahedron Lett.* 1991, 32(39), 5309-5312) were prepared by literature methods.

Example 1

Bis(9,9'-spirobifluoren-2-yl) ketone

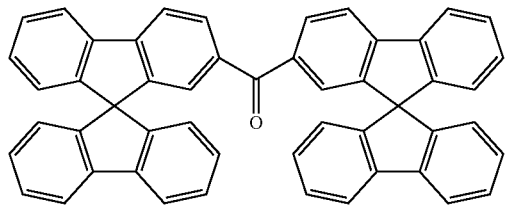

A: 2-cyano-9,9'-spirobifluorene

A suspension of 158.1 g (0.4 mol) of 2-bromo-9,9'-spirobifluorene and 89.6 g (1 mol) of copper(I) cyanide in 1100 ml of NMP was heated to 160° C. for 16 h. After cooling to 30° C., the mixture was admixed with 1000 ml of saturated ammonia solution and stirred for a further 30 min. The precipitate was filtered off with suction, washed three times with 300 ml of saturated ammonia solution and three times with 300 ml of water, and suction-dried. After the solid had been dissolved in 1000 ml of dichloromethane, the solution was dried over sodium sulfate, filtered through silica gel and concentrated to dryness. The thus obtained crude product was recrystallized once from dioxane:ethanol (400 ml:750 ml). After the crystals had been dried under reduced pressure at 80° C., 81.0 g (237 mmol), corresponding to 59.3% of theory, were obtained.

$^1$H NMR (CDCl$_3$): δ [ppm]=7.92-7.85 (m, 4 H), 7.66-7.65 (m, 1 H), 7.44-7.39 (m, 3 H), 7.22-7.19 (m, 1 H), 7.15-7.11 (m, 2 H), 6.99-6.98 (M, 1 H), 6.79-6.78 (m, 1 H), 6.69-6.67 (m, 2 H).

B: Bis(9,9'-spirobifluoren-2-yl) ketone

From a solution of 98.8 g (250 mmol) of 2-bromo-9,9'-spirobifluorene and 6 ml of 1,2-dichloroethane in 1000 ml of THF and 7.1 g (290 mmol) of magnesium, the corresponding Grignard reagent was prepared at boiling. A solution of 85.4 g (250 mmol) of 2-cyano-9,9'-spirobifluorene in a mixture of 300 ml THF and 1000 ml of toluene was added dropwise at 0-5° C. to this Grignard solution over 15 min. Subsequently, the mixture was heated under reflux for 6 h. After cooling, a mixture of 35 ml of 10N HCl, 400 ml of water and 600 ml of ethanol was slowly added dropwise. After stirring at room temperature for 16 h, the solid was filtered off with suction and washed three times with 200 ml of ethanol. The solid was recrystallized four times from NMP (5 ml/g) and subsequently sublimed under high vacuum (T=385° C., p=5×10$^{-5}$ mbar). The yield at a purity of >99.9% by HPLC was 52.1 g (79 mmol), corresponding to 31.6% of theory.

$T_g$=165° C., $T_m$=385° C.

$^1$H NMR (CDCl$_3$): δ [ppm]=7.87-7.85 (m, 2H), 7.83-7.81 (m, 4H), 7.78-7.86 (m, 2H), 7.60-7.58 (m, 2H), 7.39-7.34 (m, 6H), 7.18-7.17 (m, 2H), 7.16-7.13 (m, 2H), 7.10-7.07 (m, 4H), 6.34-6.32 (m, 2H), 6.70-6.69 (m, 4H).

Example 2

2,2'-bis(benzoyl)spiro-9,9'-bifluorene

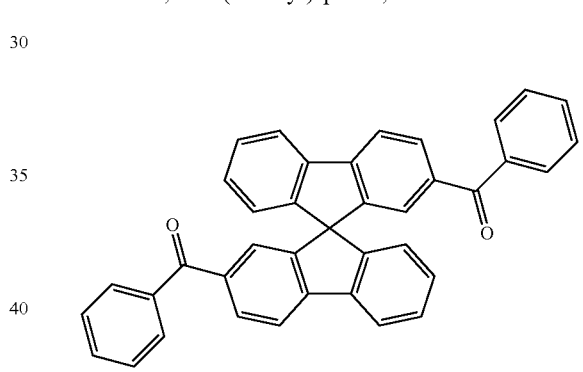

A suspension of 160.0 g (1.2 mol) of anhydrous aluminum chloride in 600 ml of 1,2-dichloroethane was admixed dropwise with good stirring with 132 ml (1.1 mol) of benzoyl chloride. A solution of 158.2 g (0.5 mol) of spiro-9,9'-bifluorene in 600 ml of 1,2-dichloroethane was added dropwise to this mixture at such a rate that the temperature did not exceed 25° C. After full addition, the mixture was stirred at room temperature for another 1 h. Subsequently, the reaction mixture was poured onto an efficiently stirred mixture of 1000 g of ice and 260 ml of 2N hydrochloric acid. The organic phase was removed and washed twice with 500 ml of water. After the organic phase had been concentrated to a volume of approx. 200 ml and 500 ml of ethanol had been added, the fine crystalline precipitate which had formed was filtered off with suction and washed with ethanol. The solid was recrystallized repeatedly from toluene and subsequently sublimed under high vacuum (T=290° C., p=5×10$^{-5}$ mbar). The yield at a purity of >99.9% by HPLC was 191.5 g (365 mmol), corresponding to 73.0% of theory.

$T_g$=99° C., $T_m$=281° C.

$^1$H NMR (CDCl$_3$): δ [ppm]=7.90 (m, 4H), 7.78 (m, 2H), 7.67 (m, 4H), 7.51 (m, 2H) 7.43-7.37 (m, 6H), 7.31 (m, 2H), 7.20 (m, 2H), 6.78 (m, 2H)

Example 3

2,2'-bis(2-fluorobenzoyl)spiro-9,9'-bifluorene

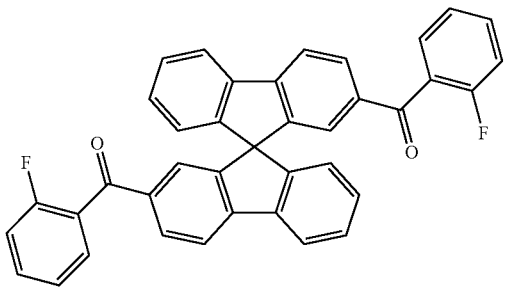

Procedure analogous to example 2. Use of 174.4 g (1.1 mol) of 2-fluorobenzoyl chloride. The solid was recrystallized repeatedly from butanone and toluene and subsequently sublimed under high vacuum (T=250° C., p=5×10$^{-5}$ mbar). The yield at a purity of >99.9% by HPLC was 192.8 g (344 mmol), corresponding to 68.8% of theory.

$T_g$=96° C., $T_m$=228° C.

$^1$H NMR (CDCl$_3$): δ [ppm]=7.90 (m, 4H), 7.77 (m, 2H), 7.48-7.40 (m, 6H), 7.37 (m, 2H), 7.21-7.18 (m, 4H), 7.09 (m, 2H) 6.77 (M, 2H).

$^{19}$F {$^1$H} NMR (CDCl$_3$): δ [ppm]=−111.7 (s)

Example 4

2.7-bis(2-spiro-9,9'-bifluorenylcarbonyl)spiro-9,9'-bifluorene

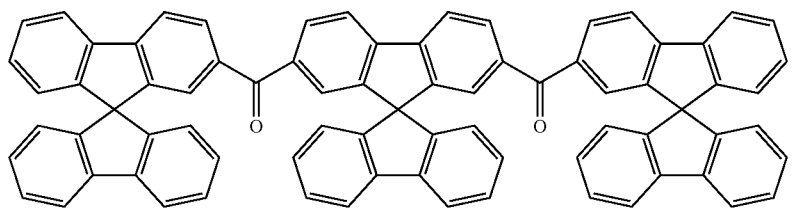

Procedure analogous to example 1B. Use of 59.3 g (125 mmol) of 2,7-dibromospiro-9,9'-bifluorene. Sublimation at T=410° C. Yield 77.1 g (77 mmol), corresponding to 61.6% of theory.

$T_g$=209° C., $T_m$=401° C.

$^1$H NMR (CDCl$_3$): δ [ppm]=7.87-7.75 (m, 12H), 7.61-7.56 (m, 4H), 7.40-7.34 (m, 8H), 7.18-7.14 (m, 6H), 7.11-7.07 (m, 6H), 6.74-6.67 (m, 8H).

Example 5

2,2'-bis(2-spiro-9,9'-bifluorenyl-carbonyl)spiro-9,9'-bifluorene

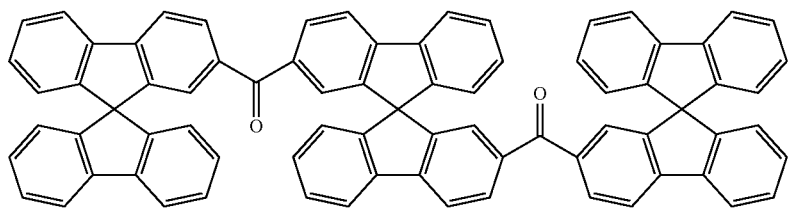

A: 9,9'-spirobifluorene-2,2'-dicarboxamide 220 ml of an ammonia solution (2N in ethanol) were admixed dropwise with good stirring with 44.1 g (100 mmol) of 9,9'-spirobifluorene-2,2'-dicarbonyl chloride dissolved in 200 ml of dioxane. After the exothermic reaction had abated, the mixture was stirred for a further 2 h, and the precipitated solid was filtered off, washed once with a mixture of 100 ml of water and 100 ml of EtOH, and once with 200 ml of ethanol, and dried under reduced pressure. The yield at a purity of >99.0% by $^1$H NMR was 37.4 g (93 mmol), corresponding to 93.0% of theory.

$^1$H NMR (DMSO-d6): δ [ppm]=8.13-8.10 (m, 4H), 8.01-7.99 (m, 2H), 7.89 (br. s, 2H, NH$_2$), 7.47-7.44 (m, 2H), 7.23 (br. s, 2H, NH$_2$), 7.22-7.18 (m, 2H), 7.14 (s, 2H), 6.66-6.64 (m, 2H)

B: 2,2'-dicyanospiro-9,9'-bifluorene

A suspension, cooled to −10° C., of 36.2 g (90 mmol) of 9,9'-spirobifluorene-2,2'-dicarboxamide in 800 ml of DMF was admixed dropwise with 52.5 ml (720 mmol) of thionyl chloride at such a rate that the temperature did not rise above −5° C. The reaction mixture was stirred at −10° C. for a further 3 h and then poured into a mixture of 2 kg of ice and 500 ml of water. The hydrolyzate was extracted twice with 500 ml each time of dichloromethane. The combined organic phases were washed with 500 ml of water and with 500 ml of sat. sodium chloride solution and dried over magnesium sulfate. The oil obtained after concentration of the organic phase crystallized after addition of 300 ml of ethanol in the form of white needles. The yield at a purity of >99.0% by $^1$H NMR was 29.4 g (80 mmol), corresponding to 89.3% of theory.

$^1$H NMR (CDCl$_2$CDCl$_2$): δ [ppm]=7.95 (d, 2H), 7.92 (d, 2H) 7.71 (dd, 2H), 7.47 (ddd, 2H), 7.24 (ddd, 2H), 6.96 (d, 2H), 6.75 (d, 2H).

C: 2,2'-bis(2-spiro-9,9'-bifluorenylcarbonyl)spiro-9,9'-bifluorene

Procedure analogous to example 1B. Use of 59.3 g (150 mmol) of 2-bromo-9,9'-spirobifluorene and 27.5 g (75 mmol) of 2,2'-dicyanospiro-9,9'-bifluorene. Sublimation at T=440° C. Yield 41.2 g (41 mmol), corresponding to 54.8% of theory.

T$_g$=213° C., T$_m$=430° C.

$^1$H NMR (CDCl$_3$): δ [ppm]=7.89-7.86 (m, 4H) 7.82-7.78 (m, 8H), 7.60 (br. m, 4H), 7.41-7.34 (m, 8H), 7.18-7.14 (m, 8H), 7.12-7.08 (4H), 6.75-6.70 (m, 8H).

Example 6

Bis(9,9'-spirobifluoren-2-yl)-N-tert-butylimine

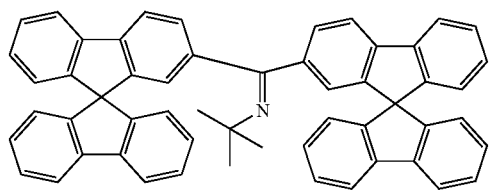

200 ml (200 mmol) of a 2M solution of titanium tetrachloride in toluene were added dropwise over 30 min to a suspension, cooled to 0° C., of 65.8 g (100 mmol) of bis(9,9'-spirobifluoren-2-yl) ketone (see example 1 for preparation) in a mixture of 105.0 ml (1 mol) of tert-butylamine and 1500 ml of toluene. Subsequently, the cooling bath was removed, and the reaction mixture, after attainment of room temperature, was stirred for a further 3 h and then heated under reflux for 60 h. After cooling, 1500 ml of diethyl ether were added and the mixture was stirred at room temperature for a further 12 h. The suspension was filtered through silica gel, and the filtrate was concentrated to dryness, taken up in 2000 ml of chloroform and filtered again through silica gel. The solid which remained after removal of the chloroform was recrystallized four times from dioxane/ethanol (1:2 vv, 10 ml/g) and subsequently sublimed under high vacuum (T=375° C., p=5×10$^{-5}$ mbar). The yield at a purity of >99.9% by HPLC was 47.8 g (67 mmol), corresponding to 67.0% of theory.

T$_g$=187° C., T$_m$=369° C.

$^1$H NMR (CDCl$_3$): δ [ppm]=7.89-7.72 (m, 7H), 7.62 (d, 1H) 7.37-7.26 (m, 7H), 7.11-7.01 (m, 7H), 6.98 (s, 1H), 6.71 (d, 1H), 6.64-6.59 (m, 5H), 6.44 (s, 1H), 0.83 (s, 9H).

Example 7

Bis(9,9'-spirobifluoren-2-yl)-N-phenylimine

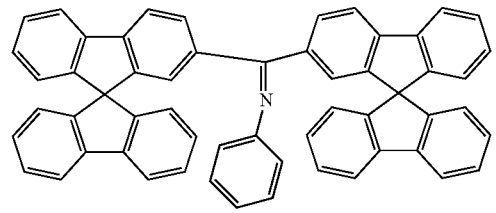

Procedure analogous to example 6. Use of 45.6 ml (500 mmol) of aniline. Sublimation at T 370° C. Yield 53.7 g (73 mmol), corresponding to 73.2% of theory.

T$_g$=159° C., T$_m$=339° C.

$^1$H NMR (CDCl$_3$): δ [ppm]=7.82-7.74 (m, 6H), 7.70 (d, 1H), 7.65 (d, 1H), 7.44 (s, 1H), 7.38-7.29 (m, 7H), 7.12-7.02 (m, 7H), 6.83 (t, 2H), 6.72-6.64 (m, 5H), 6.52 (d, 2H), 6.38 (s, 1H), 6.30 (d, 2H).

2. Production of Organic Electroluminescent Devices which Comprise Inventive Mixtures OLEDs were produced by the general process outlined below. This of course had to be adjusted in the individual case to the particular circumstances (for example layer thickness variation to achieve optimal efficiency and color).

Inventive electroluminescent devices may be produced, for example, as follows:

1. ITO-coated substrate: the substrate used is preferably ITO-coated glass with a minimum level of or no ionic impurities, for example flat glass from Merck-Balzers or Akaii. However, it is also possible to use other ITO-coated transparent substrates, for example flexible plastics films or laminates. The ITO has to combine a maximum conductivity with a high transparency. ITO layer thicknesses between 50 and 200 nm have been found to be particularly suitable. The ITO coating has to have maximum flatness, preferably with a roughness below 2 nm. The substrates are initially precleaned with 4% Dekonex solution in deionized water. Afterward, the ITO-coated substrate is either treated with ozone for at least 10 minutes or with oxygen plasma for a few minutes, or irradiated with an excimer lamp for a short time.

2. Hole injection layer (Hole Injection Layer=HIL): the HIL used is either a polymer or a low molecular weight substance. Particularly suitable polymers are polyaniline (PANI) or polythiophene (PEDOT) and derivatives thereof. They are usually 1 to 5% aqueous dispersions which are applied in thin layers of layer thickness between 20 and 200 nm, preferably between 40 and 150 nm, to the ITO substrate by spincoating, inkjet printing or other coating processes. Afterward, the PEDOT- or PANI-coated ITO substrates are dried. For the drying, several processes are possible. Conventionally, the films are dried in a drying oven between 110 and 200° C., preferably between 150 and 180° C., for from 1 to 10 minutes. However, newer drying processes, for example irradiation with IR (infrared) light, also lead to very good results, the irradiation time generally lasting only a few seconds. The low molecular weight materials used are preferably thin layers between 5 and 30 nm of copper-phthalocyanine (CuPc). Conventionally, CuPc is applied by vapor deposition in vacuum sublimation units. All HILs have to not only inject holes very efficiently, but also adhere very securely to ITO and glass; this is the case both for CuPc and for PEDOT and PANI. A particularly low absorption in the visible region and thus a high transparency is exhibited by PEDOT and PANI, which is a further necessary property of the HIL.

3. One or more hole transport layers (Hole Transport Layer=HTL): in most OLEDs, one or more HTLs are a prerequisite for good efficiency and high stability. Very good results are achieved with a combination of two layers, for example consisting of triarylamines such as MTDATA (4,4',4"-tris(N-3-methylphenyl-N-phenylamino)triphenylamine) or NaphDATA (4,4',4"-tris(N-1-naphthyl-N-phenylamino)triphenylamine) as the first HTL and NPB (N,N'-di(naphth-1-yl)-N,N'-diphenylbenzidine) or spiro-TAD (tetrakis(2,2',7,7'-diphenylamino)spiro-9,9'-bifluorene) as the second HTL. MTDATA or NaphDATA bring about an increase in the efficiency in most OLEDs by approx. 20-40%; owing to the higher glass transition temperature $T_g$, preference is given to NaphData ($T_g$=130° C.) over MTDATA ($T_g$=100° C.). As the second layer, preference is given to spiro-TAD ($T_g$=130° C.) over NPB ($T_g$=95° C.) owing to the higher $T_g$. MTDATA and NaphDATA have a layer thickness between 5 and 100 nm, preferably between 10 and 60 nm, more preferably between 15 and 40 nm. For thicker layers, somewhat higher voltages are required in order to achieve the same brightness; at the same time, the number of defects is reduced. spiro-TAD and NPB have a layer thickness between 5 and 150 nm, preferably between 10 and 100 nm, more preferably between 20 and 60 nm. With increasing layer thickness of NPB and most other triarylamines, higher voltages are required for equal brightnesses. However, the layer thickness of spiro-TAD has only a slight influence on the characteristic current-voltage electroluminescence lines, i.e. the required voltage to achieve a particular brightness depends only slightly upon the spiro-TAD layer thickness. Instead of low molecular weight triarylamines, it is also possible to use high molecular weight triarylamines. These are usually 0.1 to 30% solutions which are applied in thin layers between 20 and 500 nm, preferably between 40 and 150 nm of layer thickness, to the ITO substrate or the HIL (e.g. PEDOT or PANI layer) by spincoating, inkjet printing or other coating processes.

4. Emission Layer (Emission Layer=EML): this layer may partly coincide with layers 3 and/or 5. It consists, for example, of a low molecular weight matrix material and a low molecular weight guest material, the phosphorescent dopant, for example CBP or one of the above-described matrix materials A as the matrix material and Ir(PPy)$_3$ as the dopant. Good results are achieved at a concentration of 5-30% of Ir(PPy)$_3$ in CBP or in one of the above-described matrix materials A at an EML layer thickness between 10 and 100 nm, preferably between 10 and 50 nm. Instead of low molecular weight light-emitting compounds, it is also possible to use high molecular weight light-emitting compounds (polymers), in which case one or else both components of the host-guest system may be high in molecular weight.

5. An electron transport and hole blocking layer (Hole Blocking Layer=HBL): effective HBL materials have been found to be particularly BCP (2,9-dimethyl-4,7-diphenyl-1, 10-phenanthroline=bathocuproin) or BAlq. Instead of low molecular weight HBLs, it is also possible to use high molecular weight HBLs. However, it has been found that OLEDs which comprise inventive mixtures still exhibit very good results even without such a hole blocking layer. Therefore, a hole blocking layer was not used in all examples described below.

6. Electron transport layer (Electron Transport Layer=ETL): metal hydroxyquinolates are very suitable as ETL materials; particularly aluminum tris-8-hydroxyquinolate (AlQ$_3$) has been found to be one of the most stable electron conductors. Instead of low molecular weight ETLs, it is also possible to use high molecular weight ETLs. However, it has been found that OLEDs which comprise inventive mixtures still exhibit very good results, in particular very low voltages and high power efficiencies, even without such a hole blocking layer. Therefore, an electron transport layer was not used in all examples described below.

7. Electron injection layer (Electron Injection Layer=EIL): a thin layer having a layer thickness between 0.2 and 8 nm, preferably between 0.5 and 5 nm, consisting of a material having a high dielectric constant, in particular inorganic fluorides and oxides, for example LiF, Li$_2$O, BaF$_2$, MgO, NaF and further materials, has been found to be particularly good as the EIL. Especially in combination with Al, this additional layer leads to a distinct improvement in the electron injection and thus to improved results with regard to lifetime, quantum efficiency and power efficiency.

8. Cathode: here, generally metals, metal combinations or metal alloys having a low work function are used, for example Ca, Ba, Cs, K, Na, Mg, Al, In, Mg/Ag.

9. a) Preparation of thin layers (2.-8.) of low molecular weight compounds: all low molecular weight materials of the HIL, HTL, EML, HBL, ETL, EIL and cathode are applied by vapor deposition in vacuum sublimation units at a pressure of less than $10^{-5}$ mbar, preferably less than $10^{-6}$ mbar, more preferably less than $10^{-7}$ mbar. The vapor deposition rates may be between 0.01 and 10 nm/s, preferably 0.1 and 1 nm/s. More recent processes such as OPVD (organic physical vapor deposition) or LITI (light induced thermal imaging) are likewise suitable for the coating of low molecular weight materials, as are further printing techniques. For doped layers, OPVD has great potential because it is possible particularly efficiently to set any desired mixing ratios. It is likewise possible to continuously change the concentration of the dopants. Thus, the prerequisites for improvement in the electroluminescent device are optimal for OPVD. As described above, the preparation of the inventive devices can also be carried out by specific printing processes (such as the LITI mentioned). This has advantages both with regard to the scalability of manufacture and with regard to the setting of mixing ratios in blend layers used. For this purpose, it is, though, generally necessary to prepare appropriate layers (for LITI: transfer layers) which are only then transferred to the actual substrate.

b) Production of thin layers (2.-6.) of high molecular weight compounds (polymers): these are usually 0.1 to 30% solutions or dispersions which are applied in thin layers between 10 and 500 nm, preferably between 10 and 80 nm, of layer thickness to the ITO substrate or layers below it by spincoating, inkjet printing, LITI or other coating processes and printing techniques.

10. Encapsulation: effective encapsulation of the organic layers including the EIL and the cathode is indispensable for organic electroluminescent devices. When the organic display is formed on a glass substrate, there are several options. One option is to adhesive-bond the entire structure to a second glass or metal plate. Two-component or UV-curing epoxy adhesives have been found to be particularly suitable. The electroluminescent device may be adhesive-bonded fully or else only at the edge. When the organic display is adhesive-bonded only at the edge, the durability can be additionally improved by adding what is known as a getter. This getter consists of a very hygroscopic material, especially metal oxides, for example BaO, CaO, etc., which binds ingressing water and water vapors. An additional binding of oxygen is achieved with getter materials, for example Ca, Ba, etc. In the case of flexible substrates, particular attention should be paid to a high diffusion barrier against water and oxygen. Here, especially laminates composed of alternating thin plastics and inorganic layers (e.g. $SiO_x$ or $SiN_x$) have been found to be useful.

3. Device Examples

Here, the results of different OLEDs are compared. The basic structure, such as the materials used, degree of doping and their layer thicknesses, was identical for the example experiments for better comparability. Exclusively the host material in the emitter layer was changed, and the examples were carried out with different triplet emitters.

The first example describes a comparative standard according to the prior art, in which the emitter layer consists of the host material CBP and the guest material Ir(PPY)$_3$ (synthesized according to WO 02/060910). In addition, an OLED with an emitter layer consisting of the host material bis(9, 9'-spirobifluoren-2-yl) ketone and the guest material Ir(PPy)$_3$ is described. The second example describes a further comparison between CBP and bis(9,9'-spirobifluoren-2-yl) ketone (see example 1) with the red emitter Ir(BTP)$_3$ (synthesized according to WO 02/060910). The third example describes two OLEDs, one a deep red emitter Ir(piq)$_3$ with bis(9,9'-spirobifluoren-2-yl) ketone and the other a red emitter Ir(FMepiq)$_3$ with bis(9,9'-spirobifluoren-2-yl) ketone.

Analogously to the abovementioned general process, green- and red-emitting OLEDs with the following structure were obtained:

| | |
|---|---|
| PEDOT | 60 nm (spincoated from water; PEDOT purchased from H. C. Starck; poly[3,4-ethylenedioxy-2,5-thiophene]) |
| NaphDATA | 20 nm (applied by vapor deposition; NaphDATA purchased from SynTec; 4,4',4"-tris(N-1-naphthyl-N-phenylamino)-triphenylamine) |
| S-TAD | 20 nm (applied by vapor deposition; S-TAD prepared according to WO 99/12888; 2,2',7,7'-tetrakis(diphenylamino)spirobifluorene) |
| Emitter layer: | |
| CBP | 20 nm (applied by vapor deposition; CBP purchased from ALDRICH and purified further, finely sublimed twice more; 4,4'-bis(N-carbazolyl)biphenyl) (comparative standard) |
| OR: | |
| bis(9,9'-spirobifluoren-2-yl) ketone | 20 nm (applied by vapor deposition, synthesized and purified according to example 1), in each case doped with 10% triplet emitter |
| Ir(PPy)$_3$ | (applied by vapor deposition) |
| OR: | |
| Ir(BTP)$_3$ | (applied by vapor deposition) |
| OR: | |
| Ir(piq)$_3$ | (applied by vapor deposition) |
| OR: | |
| Ir(FMepiq)$_3$ | (applied by vapor deposition) |
| Bathocuproin (BCP) | 10 nm (applied by vapor deposition; BCP purchased from ABCR, used as obtained; 2,9-dimethyl-4,7-diphenyl-1,10-phenanthroline); not used in all examples |
| AlQ$_3$ | 10 nm (applied by vapor deposition; AlQ$_3$ purchased from SynTec; tris(quinolinolato)-aluminum(III)), not used in all examples |
| Ba-Al | 3 nm of Ba, 150 nm of Al thereon as the cathode |

These OLEDs which were yet to be optimized were characterized in a standard manner; for this purpose, the electroluminescence spectra, the efficiency (measured in Cd/A) as a function of the brightness, calculated from current-voltage-brightness characteristic lines (IUL characteristic lines), and the lifetime were determined.

For an overview, the triplet emitters used and the host materials used are depicted below:

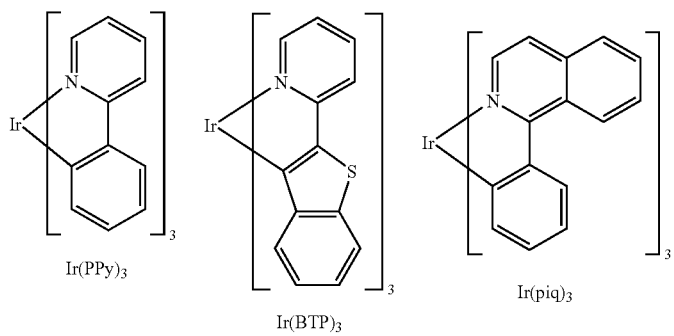
Ir(PPy)₃
Ir(BTP)₃
Ir(piq)₃
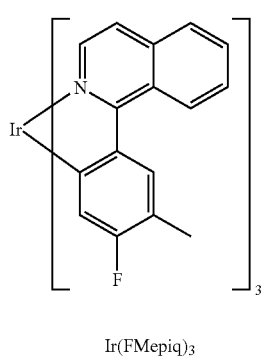
Ir(FMepiq)₃
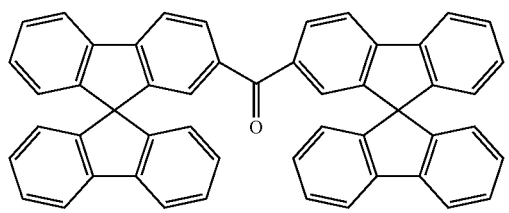
bis(9, 9′-spirobifluoren-2-yl) ketone
matrix material M1
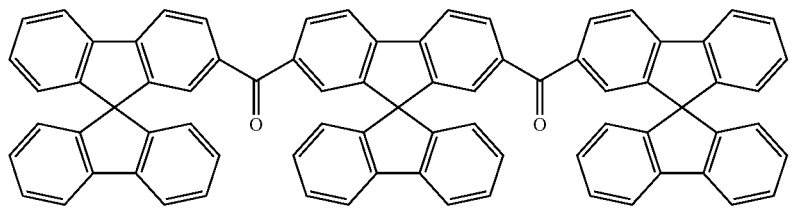
matrix material M2
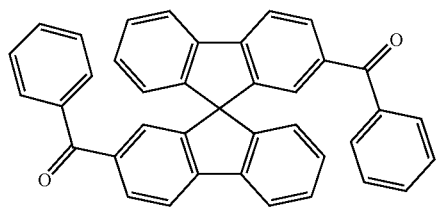
matrix material M3
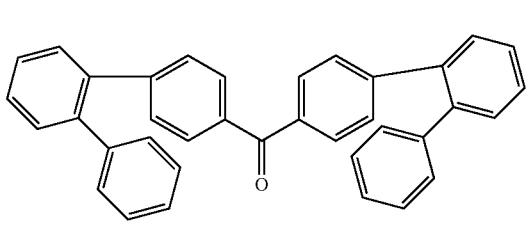
matrix material M4
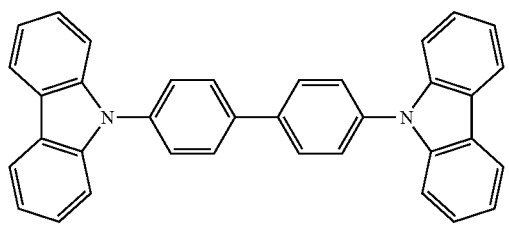
CBP
(comparative matrix material)

Use Example 1

Ir(PPy)$_3$

Electroluminescence Spectra:

The OLEDs, both the comparative standard OLED with CBP and OLED with bis(9,9'-spirobifluoren-2-yl) ketone as host material, exhibit green emission, resulting from the Ir(PPy)$_3$ dopant.

Efficiency as a Function of Brightness:

For OLEDs produced with the CBP host material, a maximum efficiency of about 25 cd/A is typically obtained, and, for the reference illumination density of 100 cd/m$^2$, 4.8 V are required. In contrast, OLEDs produced with the bis(9,9'-spirobifluoren-2-yl) ketone host material exhibit a maximum efficiency of above 30 cd/A, while the required voltage for the reference illumination density of 100 cd/m$^2$ falls even to 4.6 V. The efficiency is quite especially high when neither a pole blocking layer (HBL) nor an electron transport layer (ETL) is used, and the doped emission layer (EML) extends as far as the cathode. A maximum efficiency of above 35 cd/A is achieved, while the required voltage for the reference illumination density of 100 cd/m$^2$ falls even below 3 V. Particularly the power efficiency increases with use of bis(9,9'-spirobifluoren-2-yl) ketone as the host material (π) compared to CBP (♦) as the host material by from 20% to 100% (FIG. 1). Quite especially high power efficiencies up to 50 lm/W (□) are obtained when neither a hole blocking layer (HBL) nor an electron transport layer (ETL) is used, and the doping of the emission layer (EML) extends as far as the cathode.

Figure 2:
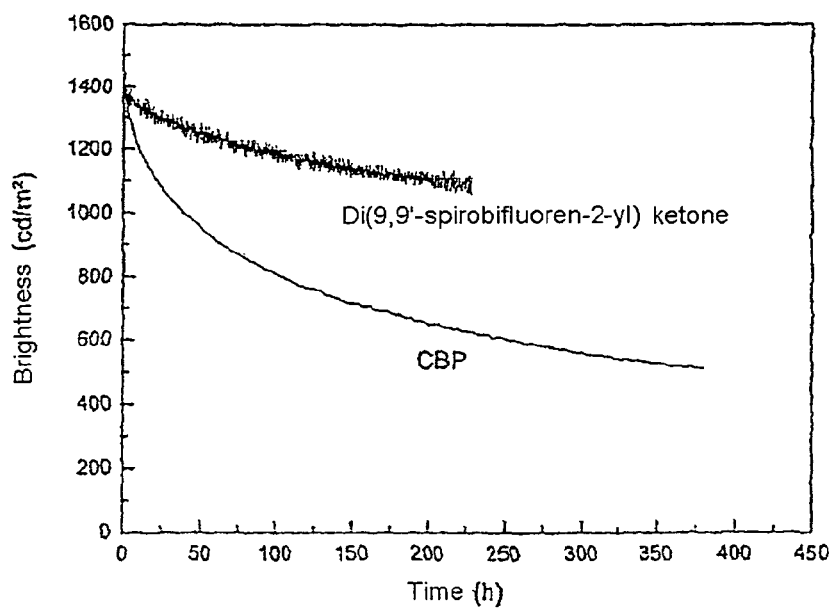
FIG. 2 illustrates two lifetime curves with CBP and with bis(9,9'-spirobifluoren-2-yl) ketone as host materials (both used here with hole blocking and electron transport layer) were shown in the same figure for better comparability. The figure shows the profile of the illumination densities, measured in cd/m$^2$, with time.

Lifetime Comparison:

The two lifetime curves (FIG. 2) with CBP and with bis(9,9'-spirobifluoren-2-yl) ketone as host materials (both used here with hole blocking and electron transport layer) were shown in the same figure for better comparability. The figure shows the profile of the illumination densities, measured in cd/m$^2$, with time. The lifetime refers typically to the time after which only 50% of the initial illumination density is attained.

With CBP as the host material, a lifetime of approx. 150 hours is obtained at a starting brightness of 1400 cd/m$^2$, which corresponds to an accelerated measurement, since the starting brightness is distinctly above the brightness which is required for typical active matrix-addressed display applications (250 cd/m$^2$). For bis(9,9'-spirobifluoren-2-yl) ketone, at the same starting brightness, a lifetime of approx. 2000 hours is achieved, which corresponds to an increase in the lifetime by about 1300%; this is also the case when neither a hole blocking layer (HBL) nor an electron transport layer (ETL) is used.

From these measured lifetimes, lifetimes can then be calculated for a starting brightness of 250 cd/m$^2$. In the case of the CBP host material, only a lifetime of 4700 hours is obtained, which is distinctly below the required 10 000 hours for a display application. In contrast, with bis(9,9'-spirobifluoren-2-yl) ketone, a lifetime of over 60 000 hours is achieved, which significantly exceeds the minimum requirements.

Use Example 2

Ir(BTP)$_3$

Analogous experiments were carried out with a red triplet emitter Ir(BTP)$_3$.

Figure 3:
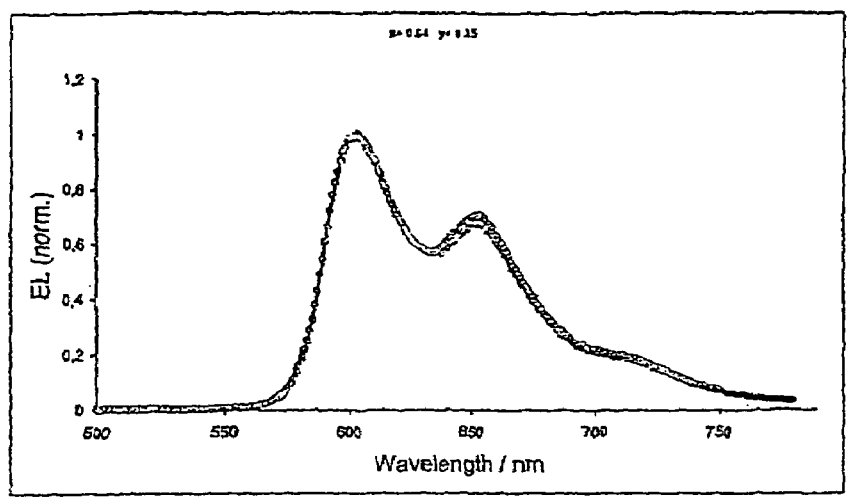
FIG. 3 illustrates two electroluminescence spectra.

Electroluminescence Spectra:

The OLEDs, both of the comparative standard OLED with CBP and the OLED with bis(9,9'-spirobifluoren-2-yl) ketone as the host material, exhibit red emission resulting from the Ir(BTP)$_3$ dopant. The two spectra are shown in FIG. 3.

Figure 4:
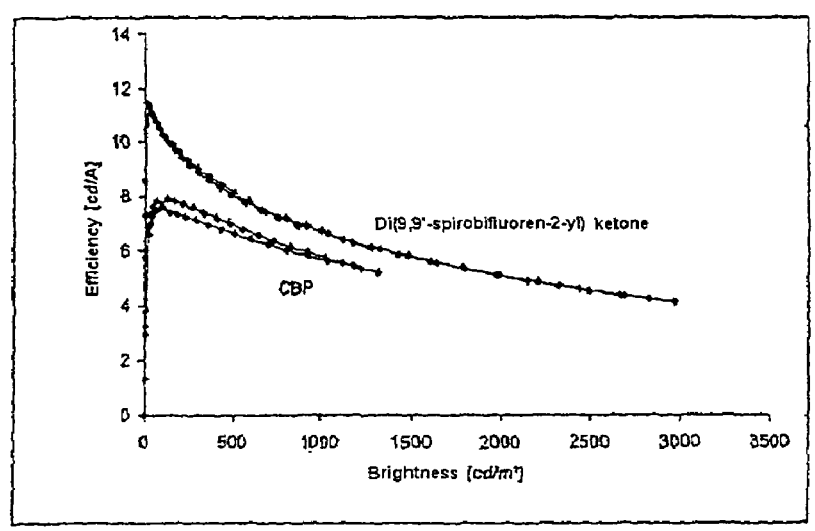
FIG. 4 illustrates efficiency as a function of brightness.

Efficiency as a Function of Brightness:

For OLEDs produced with the CBP host material, typically a maximum efficiency of about 8 cd/A and, for the reference illumination density of 100 cd/m$^2$, 6.2 V are required. In contrast, OLEDs produced with the host material bis(9,9'-spirobifluoren-2-yl) ketone exhibit a maximum efficiency of above 11 cd/A, while the required voltage for the reference illumination density of 100 cd/m$^2$ falls even to 5.2 V (FIG. 4).

Figure 5:
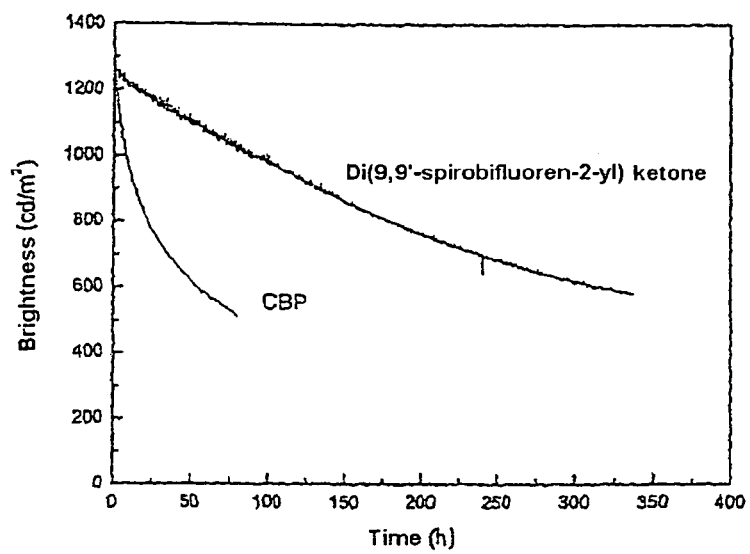
FIG. 5 illustrates two lifetime curves. The figure shows the profile of the illumination density, measured in cd/m$^2$, with time.

Lifetime Comparison:

For better comparability, the two lifetime curves (FIG. 5) are shown in the same figure. The figure shows the profile of the illumination density, measured in cd/m$^2$, with time.

With CBP as the host material, a lifetime of approx. 53 hours is obtained at a starting brightness of nearly 1300 cd/m$^2$, which in this example too corresponds to an accelerated measurement. With bis(9,9'-spirobifluoren-2-yl) ketone, a lifetime of approx. 275 hours is obtained at the same starting brightness, which corresponds to an increase in the lifetime by about 500%.

From these measured lifetimes, it is possible to calculate lifetimes for a starting brightness of 250 cd/m$^2$. In the case of the CBP host material, only a lifetime of 1600 hours is obtained, which is distinctly below the required 10 000 hours for display applications. In contrast, with bis(9,9'-spirobifluoren-2-yl) ketone, a lifetime of above 8200 hours is obtained, which closely approximates to the minimum requirement.

Use Example 3

Ir(piq)$_3$ and Ir(FMepiq)$_3$

It was likewise possible to carry out experiments with a deep red triplet emitter Ir(piq)$_3$ with bis(9,9'-spirobifluoren-2-yl) ketone and a red triplet emitter Ir(FMepiq)$_3$ with bis(9,9'-spirobifluoren-2-yl) ketone.

Figure 6:
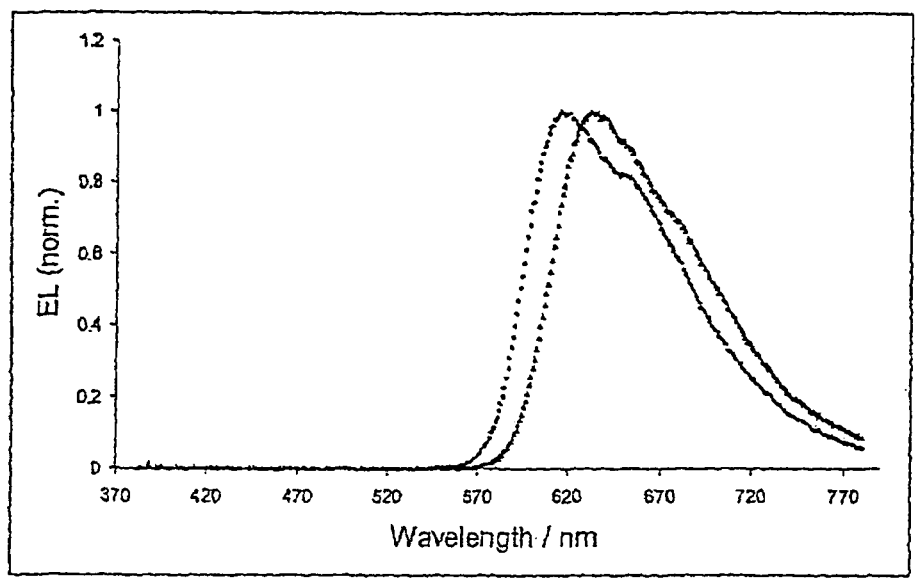
FIG. 6 illustrates two electroluminescence spectra.

Electroluminescence Spectra:

The OLEDs exhibit a deep red emission and a red emission, resulting from the dopants Ir(piq)$_3$ (π) and Ir(FMepiq)$_3$ (♦). The two spectra are shown in FIG. 6. From the spectra, the CIE color coordinates calculated for Ir(piq)$_3$ in bis(9,9'-spirobifluoren-2-yl) ketone (7t) are x=0.69; y=0.31, and those calculated for Ir(FMepiq)$_3$ in bis(9,9'-spirobifluoren-2-yl) ketone (♦) are x=0.66; y=0.34.

Figure 7:
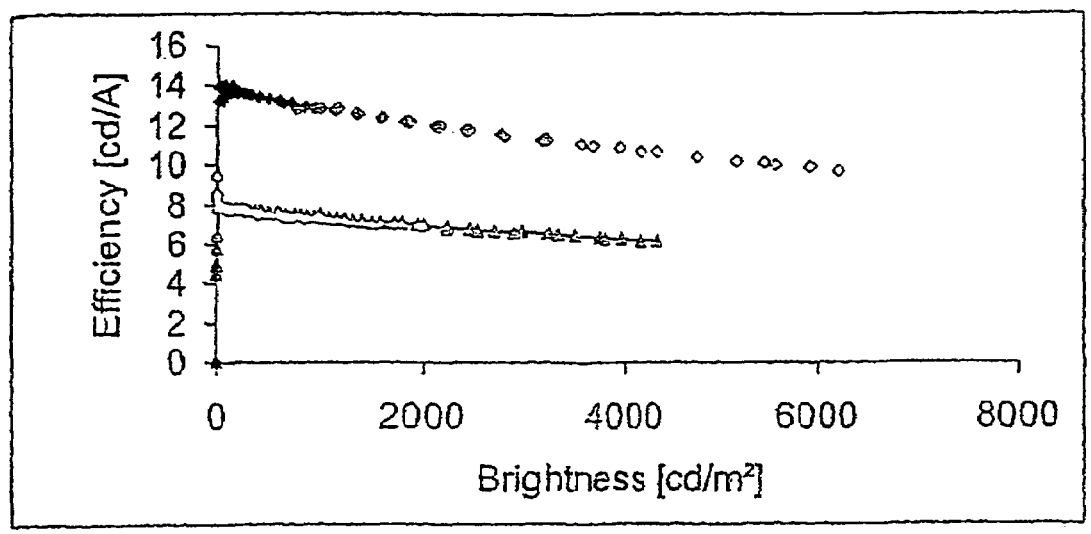
FIG. 7 illustrates efficiency as a function of brightness.

Efficiency as a Function of Brightness:

Both Ir(piq)$_3$ (π) in bis(9,9'-spirobifluoren-2-yl) ketone and Ir(FMepiq)$_3$ (♦) in bis(9,9'-spirobifluoren-2-yl) ketone exhibit a very high efficiency of max. 8 cd/A (for Ir(piq)$_3$ (π) at CIE color coordinates x=0.69, y=0.31) and 14 cd/A (for Ir(FMepiq)$_3$ (♦) at CIE color coordinates x=0.66, y=0.34) (FIG. 7). In both cases, the required voltage for 100 cd/m$^2$ fell below 6 V.

Figure 8:
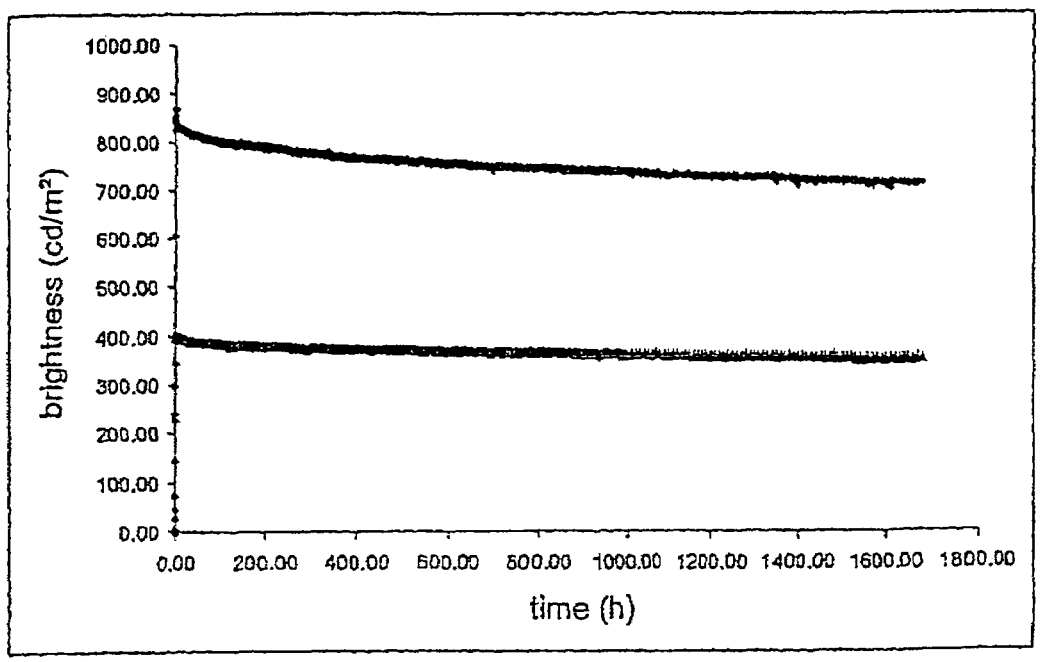
FIG. 8 illustrates the lifetime of Ir(piq)$_3$ with bis(9,9'-spirobifluoren-2-yl) ketone at constant current of 10 mA/cm$^2$ at a starting brightness of approx. 800 cd/m$^2$ and 5 mA/cm$^2$ at a starting brightness of approx. 400 cd/m$^2$.

Lifetime:

FIG. 8 shows the lifetime of Ir(piq)$_3$ with bis(9,9'-spirobifluoren-2-yl) ketone at constant current of 10 mA/cm$^2$ at a starting brightness of approx. 800 cd/r$^2$ and 5 mA/cm$^2$ at a starting brightness of approx. 400 cd/m$^2$. In this case, a decline in the brightness of approx. 10% after 1680 h at starting brightness 800 cd/m$^2$, and of approx. 5% after 1680 h at starting brightness 400 cd/m2. An extrapolation gives rise to a lifetime of from approx. 5000 h at starting brightness 800 cd/m$^2$ and 20 000 h at starting brightness 400 cd/m$^2$. For a starting brightness of 200 cd/m$^2$, a lifetime of 80 000 h is calculated. Ir(FMepiq)$_3$ in bis(9,9'-spirobifluoren-2-yl) ketone exhibits a comparable lifetime.

Further device examples are compiled in table 2 which follows, the emission stemming in each case from the corresponding emitter.

TABLE 2

| Experiment | EML | HBL | ETL | Max. efficiency (cd/A) | Max. power efficiency (Lm/W) | Voltage (V) at 100 cd/m$^2$ | Lifetime (h) at 10 mA/cm$^2$ |
|---|---|---|---|---|---|---|---|
| Comparative example for 1) | CBP: 20% Ir(ppy)$_3$ (20 nm) | BCP (10 nm) | AlQ$_3$ (10 nm) | 25 | 12 | 4.8 | 150 |
| Example 1a) | M1: 20% Ir(ppy)$_3$ (20 nm) | BCP (10 nm) | AlQ$_3$ (10 nm) | 30 | 25 | 4.6 | 400 |
| Example 1b) | M1: 20% Ir(ppy)$_3$ (60 nm) | — | — | 35 | 50 | 3.0 | 370 |
| Example 1c) | M3: 20% Ir(ppy)$_3$ (20 nm) | BCP (10 nm) | AlQ$_3$ (10 nm) | 28 | 20 | 4.5 | 250 |
| Example 1d) | M4: 20% Ir(ppy)$_3$ (20 nm) | BCP (10 nm) | AlQ$_3$ (10 nm) | 39 | 22 | 4.9 | 220 |
| Example 1e) | M4: 20% Ir(ppy)$_3$ (20 nm) | — | — | 42 | 32 | 4.5 | 200 |
| Comparative example for 2) | CBP: 20% Ir(BTP)$_3$ (20 nm) | BCP (10 nm) | AlQ$_3$ (10 nm) | 8 | 5 | 6.2 | 53 |
| Example 2a) | M1: 20% Ir(BTP)$_3$ (20 nm) | BCP (10 nm) | AlQ$_3$ (10 nm) | 11 | 8 | 5.2 | 275 |
| Example 2b) | M1: 20% Ir(BTP)$_3$ (20 nm) | — | — | 11 | 10 | 4.1 | 250 |
| Comparative example for 3) | CBP: 20% Ir(piq)$_3$ (30 nm) | BCP (10 nm) | AlQ$_3$ (10 nm) | 7 | 4 | 6.4 | 5000 (extrapolated) |
| Example 3a) | M1: 20% Ir(piq)$_3$ (30 nm) | BCP (10 nm) | AlQ$_3$ (10 nm) | 8 | 6 | 5.8 | 20 000 (extrapolated) |
| Example 3b) | M1: 20% Ir(piq)$_3$ (30 nm) | — | — | 7 | 8 | 3.2 | 15 000 (extrapolated) |
| Example 3c) | M2: 20% Ir(piq)$_3$ (30 nm) | BCP (10 nm) | AlQ$_3$ (10 nm) | 7 | 5 | 6.1 | 20 000 (extrapolated) |
| Example 4a) | M1: 20% Ir(FMepiq)$_3$ (30 nm) | BCP (10 nm) | AlQ$_3$ (10 nm) | 14 | 9 | 5.9 | 80 000 (old: purported) |
| Example 4b) | M1: 20% Ir(FMepiq)$_3$ (30 nm) | — | — | 15 | 12 | 4 | 80 000 |
| Example 4c) comparison | CBP: 20% Ir(FMepiq)$_3$ (30 nm) | BCP (10 nm) | AlQ$_3$ (10 nm) | 10 | 6 | 7 | 10 000 |

What is claimed is:

1. Mixtures comprising
   at least one matrix material A which contains a structural unit of the form C=Q in which Q has at least one non-bonding electron pair and represents the element O, S, Se or N, and
   at least one emission material B which is capable of emission and is a compound which, upon suitable excitation, emits light, and contains at least one element of atomic number greater than 20.

2. The mixture as claimed in claim 1, characterized in that the matrix material A can form glasslike layers.

3. The mixture as claimed in claim 1, characterized in that the matrix material A has a glass transition temperature $T_g$ (measured as the pure substance) greater than 70° C.

4. The mixture as claimed in claim 1, characterized in that the matrix material A used is at least one compound of the formula (1), formula (2) and/or formula (3)

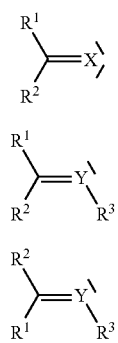

formula (1)

formula (2)

formula (3)

where the symbols and indices are each defined as follows:
   X is the same or different at each instance and is O, S or Se;
   Y at each instance is N;
   $R^1$, $R^2$ and $R^3$ are the same or different at each instance and is H, CN, a straight-chain, branched or cyclic alkyl, alkoxy or alkylamino group having from 1 to 40 carbon atoms, in which one or more nonadjacent $CH_2$ groups is optionally replaced by —$R^4C$=$CR^4$—, —C≡C—, C=O, C=S, C=Se, C=$NR^4$, —O—, —S—, —$NR^5$— or —$CONR^6$—, and in which one or more hydrogen atoms is optionally replaced by F, Cl, Br, I, or
   an aromatic or heteroaromatic system having from 1 to 40 carbon atoms, in which one or more hydrogen atoms is optionally replaced by F, Cl, Br, I, and which is optionally substituted by one or more nonaromatic $R^1$ radicals, and a plurality of substituents $R^1$ and/or $R^1$, $R^2$, either on the same ring or on the two different rings, optionally together in turn form a further mono- or polycyclic, aliphatic or aromatic ring system; with the proviso that $R^1$=$R^2$=$R^3$≠hydrogen;
   $R^4$, $R^5$ and $R^6$ are the same or different at each instance and are H or an aliphatic or aromatic hydrocarbon radical having from 1 to 20 carbon atoms.

5. The mixture as claimed in claim 1, characterized in that the matrix material A used is at least one compound of the formula (4) to (9)

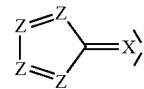

formula (4)

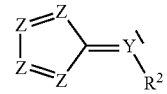

formula (5)

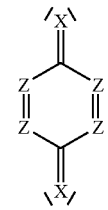

formula (6)

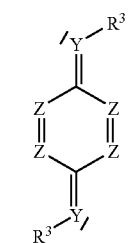

formula (7)

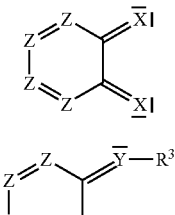

formula (8)

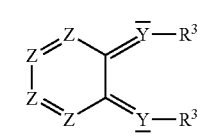

formula (9)

where
   X is the same or different at each instance and is O, S or Se;
   Y at each instance is N;
   $R^1$, $R^2$ and $R^3$ are the same or different at each instance and are H, CN, a straight-chain, branched or cyclic alkyl, alkoxy or alkylamino group having from 1 to 40 carbon atoms, in which one or more nonadjacent $CH_2$ groups is optionally replaced by —$R^4C$=$CR^4$—, —C≡C—, C=O, C=S, C=Se, C=$NR^4$, —O—, —S—, —$NR^5$— or —$CONR^6$—, and in which one or more hydrogen atoms is optionally replaced by F, Cl, Br, I, or
   an aromatic or heteroaromatic system having from 1 to 40 carbon atoms, in which one or more hydrogen atoms is optionally replaced by F, Cl, Br, I, and which is optionally substituted by one or more nonaromatic $R^1$ radicals, and a plurality of substituents $R^1$ and/or $R^1$, $R^2$, either on the same ring or on the two different rings, optionally together in turn form a further mono- or polycyclic, aliphatic or aromatic ring system; with the proviso that $R^1$=$R^2$=$R^3$≠hydrogen;

R[4], R[5] and R[6] are the same or different at each instance and are H or an aliphatic or aromatic hydrocarbon radical having from 1 to 20 carbon atoms and Z is the same or different at each instance and is CR[1] or N.

6. The mixture as claimed in claim 5, characterized in that the matrix material A used is at least one compound of the formula (1) to (9) in which the symbols used are:

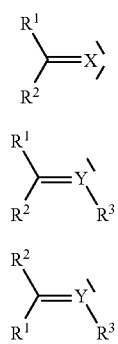

formula (1)
formula (2)
formula (3)

X is the same or different at each instance and is O or S,

Y at each instance is N;

Z at each instance is CR[1];

R[1], R[2] and R[3] are the same or different at each instance and are H, a straight-chain, branched or cyclic alkyl group which has from 1 to 40 carbon atoms and no hydrogen atoms in the α-position to the keto or imine function, in which one or more nonadjacent $CH_2$ groups is optionally replaced by —R[4]C=CR[4]—, —C≡C—, C=O, C=S, C=Se, C=NR[4], —O—, —S—, —NR[5]— or —CONR[6]—, and in which one or more hydrogen atoms is optionally replaced by F, Cl, Br, I, or an aromatic or heteroaromatic system having from 1 to 40 carbon atoms, in which one or more hydrogen atoms may be replaced by F, Cl, Br, I, and which is optionally substituted by one or more nonaromatic R[1] radicals, and a plurality of substituents R[1] and/or R[1], R[2], either on the same ring or on the different rings, optionally together in turn form a further mono- or polycyclic, aliphatic or aromatic ring system, R[4], R[5] and R[6] are the same or different at each instance and are H or an aliphatic or aromatic hydrocarbon radical having from 1 to 20 carbon atoms.

7. The mixture as claimed in claim 1, characterized in that the matrix material A used is at least one compound of the formula (10) to (15)

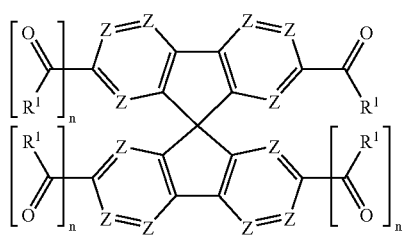

formula (10)

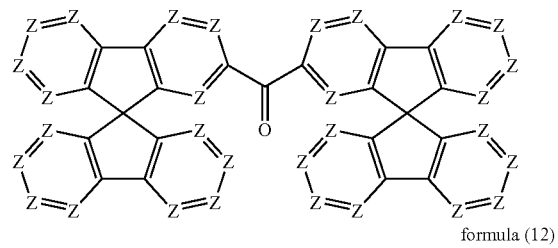

formula (11)

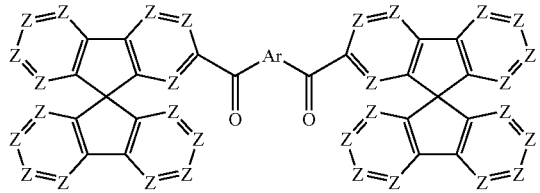

formula (12)

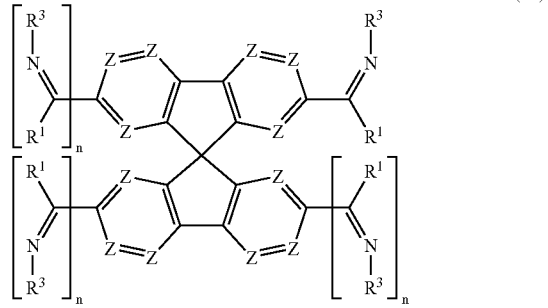

formula (13)

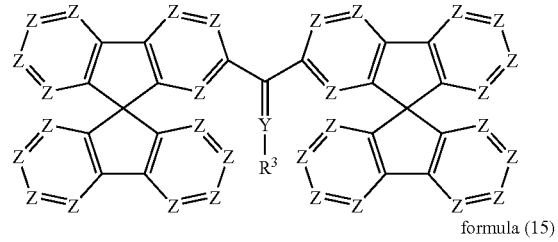

formula (14)

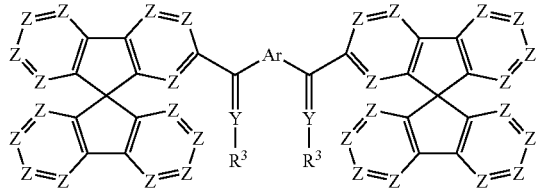

formula (15)

where

Y at each instance is N;

Z is the same or different at each instance and is CR[1] or N;

R[1], R[2] and R[3] are the same or different at each instance and are H, CN, a straight-chain, branched or cyclic alkyl, alkoxy or alkylamino group having from 1 to 40 carbon atoms, in which one or more nonadjacent $CH_2$, groups is optionally replaced by —R[4]C=CR[4]—, —C≡C—, C=O, C=S, C=Se, C=NR[4], —O—, —S—, —NR[5]— or —CONR[6]—, and in which one or more hydrogen atoms is optionally replaced by F, Cl, Br, I, or an aromatic or heteroaromatic system having from 1 to 40 carbon atoms, in which one or more hydrogen atoms is optionally replaced by F, Cl, Br, I, and which is optionally substituted by one or more nonaromatic $R^1$ radicals, and a plurality of substituents $R^1$ and/or $R^1$, $R^2$, either on the same ring or on the two different rings, optionally together in turn form a further mono- or polycyclic, aliphatic or aromatic ring system; with the proviso that $R^1=R^2=R^3\neq$hydrogen;

$R^4$, $R^5$ and $R^6$ are the same or different at each instance and are H or an aliphatic or aromatic hydrocarbon radical having from 1 to 20 carbon atoms, Ar is the same or different at each instance and is an aromatic or heteroaromatic system having from 2 to 40 carbon atoms, in which one or more hydrogen atoms is optionally replaced by F, Cl, Br, I, and which is optionally substituted by one or more nonaromatic $R^1$ radicals, and a plurality of substituents $R^1$, either on the same ring or on different rings, optionally together in turn form a further mono- or polycyclic, aliphatic or aromatic ring system;

n is the same or different at each instance and is 0 or 1.

8. The mixture as claimed in claim 1, characterized in that the emitter B used is at least one compound which, upon suitable excitation, emits light and contains at least one atom of atomic number greater than 38 and less than 84.

9. The mixture as claimed in claim 8, characterized in that the emitter B used is at least one compound which, upon suitable excitation, emits light and contains at least one atom of atomic number greater than 56 and less than 80.

10. The mixture as claimed in claim 9, characterized in that the emitter B used is at least one compound which, upon suitable excitation, emits light and contains at least one atom from the group of molybdenum, tungsten, rhenium, ruthenium, osmium, rhodium, iridium, palladium, platinum, silver, gold or europium.

11. The mixture as claimed in claim 1, characterized in that the emitter B used is at least one compound of the formula (16) to (19)

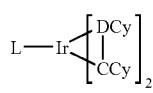
formula (16)

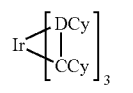
formula (17)

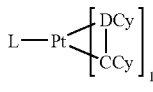
formula (18)

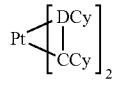
formula (19)

where the symbols used are:

DCy is the same or different at each instance and is a cyclic group which contains at least one donor atom via which the cyclic group is bonded to the metal atom, and which optionally bear one or more substituents $R^9$; the DCy and CCy groups are joined together via a covalent bond;

CCy is the same or different at each instance and is a cyclic group which contains a carbon atom via which the cyclic group is bonded to the metal and which optionally bear one or more substituents $R^9$;

$R^9$ is the same or different at each instance and is H, F, Cl, Br, I, $NO_2$, CN, a straight-chain or branched or cyclic alkyl or alkoxy group having from 1 to 40 carbon atoms, in which one or more nonadjacent $CH_2$ groups is optionally replaced by $-CR^4=CR^4-$, $-C\equiv C-$, $C=O$, $C=S$, $C=Se$, $C=NR^4$, $-O-$, $-S-$, $-NR^5-$ or $-CONR^6-$, and in which one or more hydrogen atoms is optionally replaced by F, or an aromatic or heteroaromatic system which has from 4 to 40 carbon atoms and is optionally substituted by one or more nonaromatic $R^9$ radicals; and a plurality of substituents $R^9$, either on the same ring or on the two different rings, optionally together in turn form a further mono- or polycyclic, aliphatic or aromatic ring system;

L is the same or different at each instance and is a bidentate chelating ligand;

$R^4$, $R^5$ and $R^6$ are the same or different at each instance and is H or an aliphatic or aromatic hydrocarbon radical having from 1 to 20 carbon atoms.

12. The mixture as claimed in claim 1, characterized in that the matrix material contains one or more polymers or dentrimers.

13. The mixture as claimed in claim 12, characterized in that the polymer is conjugated, semiconjugated or nonconjugated.

14. The mixture as claimed in claim 12, characterized in that the polymer is selected from the group of the polyfluorenes, poly-spiro-bifluorenes, poly-para-phenylenes, polycarbazoles, polyvinylcarbazoles, polythiophenes, or else from copolymers which have a plurality of these units.

15. The mixture as claimed in claim 1, characterized in that the mixture contains between 1 to 99% by weight of emitter B based on the overall mixture of emitter B and matrix material A.

16. An electronic component comprising at least one mixture as claimed in claim 1.

17. The electronic component as claimed in claim 16, characterized in that it is an organic light-emitting diode (OLED), an organic integrated circuit (O-IC), an organic field-effect transistor (OFET), an organic thin-film transistor (OTFT), an organic solar cell (O-SC) or an organic laser diode (O-laser).

18. The electronic component as claimed in claim 16, characterized in that the electronic component is an organic light-emitting diode (OLED) which comprises at least one hole injection layer and/or at least one hole transport layer and/or at least one hole blocking layer and/or at least one electron transport layer and/or at least one electron injection layer and/or further layers, and which comprises at least one mixture comprising at least one matrix material A which contains a structural unit of the form C=Q in which Q has at least one non-bonding electron pair and represents the element O, S, Se or N, and at least one emission material B which is capable of emission and is a compound which, upon suitable excitation, emits light, and contains at least one element of atomic number greater than 20 in the emission layer.

19. Compounds of the formula (10a) to (15)

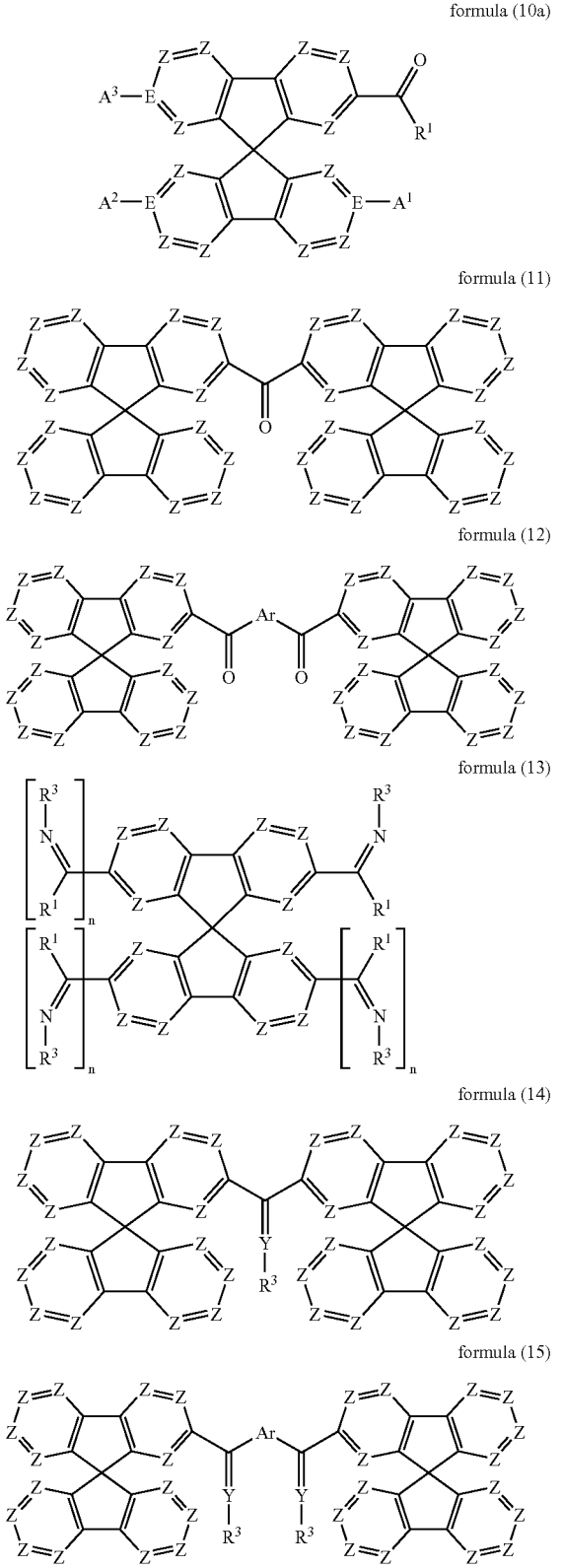

formula (10a)

formula (11)

formula (12)

formula (13)

formula (14)

formula (15)

in which the symbols

Y at each instance is N;

Z is the same or different at each instance and is $CR^1$ or N;

$R^1$, $R^2$ and $R^3$ are the same or different at each instance and are H, CN, a straight-chain, branched or cyclic alkyl, alkoxy or alkylamino group having from 1 to 40 carbon atoms, in which one or more nonadjacent $CH_2$ groups is optionally replaced by $-R^4C=CR^4-$, $-C\equiv C-$, C=O, C=S, C=Se, $C=NR^4$, $-O-$, $-S-$, $-NR^5-$ or $-CONR^6-$, and in which one or more hydrogen atoms is optionally replaced by F, Cl, Br, I, or an aromatic or heteroaromatic system having from 1 to 40 carbon atoms, in which one or more hydrogen atoms is optionally replaced by F, Cl, Br, I, and which is optionally substituted by one or more nonaromatic $R^1$ radicals, and a plurality of substituents $R^1$ and/or $R^1$, $R^2$, either on the same ring or on the two different rings, optionally together in turn form a further mono- or polycyclic, aliphatic or aromatic ring system; with the proviso that $R^1=R^2=R^3\neq$hydrogen;

$R^4$, $R^5$ and $R^6$ are the same or different at each instance and are H or an aliphatic or aromatic hydrocarbon radical having from 1 to 20 carbon atoms, Ar is the same or different at each instance and is an aromatic or heteroaromatic system having from 2 to 40 carbon atoms, in which one or more hydrogen atoms is optionally replaced by F, Cl, Br, I, and which is optionally substituted by one or more nonaromatic $R^1$ radicals, and a plurality of substituents $R^1$, either on the same ring or on different rings, optionally together in turn form a further mono- or polycyclic, aliphatic or aromatic ring system;

E is the same or different at each instance and is C or N;

$R^7$ is the same or different at each instance and is an alkyl, alkoxy or alkylamino group having from 1 to 40 carbon atoms, in which one or more $CH_2$ groups is optionally replaced by $-R^4C=CR^4-$, $-C\equiv C-$, C=O, C=S, C=Se, $C=NR^4$, $-O-$, $-S-$, $-NR^4-$ or $-CONR^4-$, and in which one or more hydrogen atoms is optionally replaced by F, Cl, Br, I, with the proviso that no hydrogen atoms are bonded in the α-position to the carbonyl group, or an aromatic group which may optionally be substituted by halogen, alkyl, trifluoromethyl, hydroxyl, $-SH$, $-S$-alkyl, alkoxy, nitro, cyano, $-COOH$, $-COO$alkyl, $-NH_2$, -Nalkyl, benzyl or benzoyl, or a larger aromatic system having from 2 to 40 carbon atoms, in which one or more hydrogen atoms is optionally replaced by F, Cl, Br, I, and which is optionally substituted by one or more nonaromatic $R^1$ radicals, and a plurality of substituents $R^1$ may in turn form a further mono- or polycyclic, aliphatic or aromatic ring system;

$A^1$ at each instance is $R^8$ or $CO-R^7$ when X=C or is a free electron pair when X=N;

$A^2$ at each instance is $R^8$ or $CO-R^7$ when X=C or is a free electron pair when X=N;

$A^3$ at each instance is $R^8$ or $CO-R^7$ when X=C or is a free electron pair when X=N;

$R^8$ is the same or different at each instance and is H, F, Cl, Br, I, CN, $NO_2$, a straight-chain or branched or cyclic alkyl group having from 1 to 40 carbon atoms, in which one or more nonadjacent $CH_2$ groups is optionally replaced by $-R^4C=CR^4-$, $-C\equiv C-$, C=S, C=Se, $C=NR^4$, $-O-$, $-S-$, $-NR^4-$ or —CONR$^4$—, and in which one or more hydrogen atoms is optionally replaced by F, Cl, Br, I, or an aromatic or heteroaromatic system having from 1 to 40 carbon atoms, in which one or more hydrogen atoms is optionally replaced by F, Cl, Br, I, and which is optionally substituted by one or more nonaromatic R$^1$ radicals, and a plurality of substituents R$^1$ and/or R$^1$/R$^4$, either on the same ring or on the different rings, optionally together in turn form a further mono- or polycyclic, aliphatic or aromatic ring system;

with the proviso that, for the compound of the formula (10a), only the following combinations are permitted for the symbols described, where R$^8$ and R$^4$ can be selected freely according to the definition:

when R$^7$ is an alkyl group without α-hydrogen atoms, the symbols Z, E, A$^1$, A$^2$ and A$^3$ can be selected freely according to the definition;

when R$^7$ is an aromatic group and at least one Z is N, the symbols E, A$^1$, A$^2$ and A$^3$ can be selected freely according to the definition;

when R$^7$ is an aromatic group and at least one Z is a CR$^1$ group where R$^1$ is other than H, the symbols E, A$^1$, A$^2$ and A$^3$ can be selected freely according to the definition;

when R$^7$ is an aromatic group and all Z are CH and at least one symbol E is N, the symbols A$^1$, A$^2$ and A$^3$ can be selected freely according to the definition;

when R$^7$ is an aromatic group, all Z are CH and all E are C, at least one of the symbols A$^1$, A$^2$ and/or A$^3$ has to be an R$^8$ group other than alkyl, while the two other groups can be selected freely according to the definition;

when R$^7$ is an aromatic group, all Z are CH, all E are C and the two symbols A$^1$ and A$^2$ are selected freely according to the definition, at least one of the two symbols being a group other than H, the symbol A$^3$ is a CO—R$^7$ group where R$^7$ here can be selected freely according to the definition;

when R$^7$ is a larger aromatic system, for example fluorene, spirobifluorene, triarylamine, etc., the symbols Z, E, A$^1$, A$^2$ and A$^3$ can be selected freely according to the definition.

20. The electronic component as claimed in claim 19, characterized in that a mixture comprising at least one matrix material A which contains a structural unit of the form C=Q in which Q has at least one non-bonding electron pair and represents the element O, S, Se or N, and at least one emission material B which is capable of emission and is a compound which, upon suitable excitation, emits light, and contains at least one element of atomic number greater than 20 without the use of a separate hole blocking layer directly adjoins an electron transport layer.

21. The electronic component as claimed in claim 19, characterized in that the mixture comprising at least one matrix material A which contains a structural unit of the form C=Q in which Q has at least one non-bonding electron pair and represents the element O, S, Se or N, and at least one emission material B which is capable of emission and is a compound which, upon suitable excitation, emits light, and contains at least one element of atomic number greater than 20 without use of a separate hole blocking layer and of a separate electron transport layer directly adjoins an electron injection layer or the cathode.

* * * * *